(12) United States Patent
Lawman et al.

US006838282B2

(10) Patent No.: US 6,838,282 B2
(45) Date of Patent: Jan. 4, 2005

(54) ANTIBODY RECOGNIZING A SMALL SUBSET OF HUMAN HEMATOPOIETIC CELLS

(75) Inventors: Michael J. P. Lawman, Chipley, FL (US); Patricia Lawman, Chipley, FL (US)

(73) Assignee: Morphogenesis, Inc., Chipley, FL (US)

( * ) Notice: Subject to any disclaimer, the term of this patent is extended or adjusted under 35 U.S.C. 154(b) by 36 days.

(21) Appl. No.: 10/299,048

(22) Filed: Nov. 18, 2002

(65) Prior Publication Data

US 2003/0228291 A1 Dec. 11, 2003

Related U.S. Application Data

(62) Division of application No. 09/873,835, filed on Jun. 4, 2001, now Pat. No. 6,482,598, which is a division of application No. 09/531,827, filed on Mar. 21, 2000, now Pat. No. 6,242,579, which is a division of application No. 08/970,032, filed on Nov. 13, 1997, now Pat. No. 6,043,348
(60) Provisional application No. 60/030,428, filed on Nov. 13, 1996.

(51) Int. Cl.[7] .................................................. C12N 5/08
(52) U.S. Cl. ...................... 435/372; 435/41; 435/325; 435/372.1; 435/372.2; 435/372.3
(58) Field of Search ........................... 435/41, 325, 372, 435/372.1, 372.2, 372.3

(56) References Cited

U.S. PATENT DOCUMENTS

| 4,714,680 A | 12/1987 | Civin |
| 5,061,620 A | 10/1991 | Tsukamoto et al. |
| 5,585,089 A | 12/1996 | Queen et al. |

FOREIGN PATENT DOCUMENTS

| BE | 0895670 | 5/1983 |
| WO | WO 93/25216 | 12/1993 |
| WO | WO 94/02157 | 2/1994 |
| WO | WO 95/03693 | 2/1995 |
| WO | WO 96/15229 | 5/1996 |

OTHER PUBLICATIONS

Bodger, M.P. et al. (1981) "A monoclonal antibody specific for immature human hemopoietic cells and T lineage cells" *Journal of Immunology*, vol. 127, No. 6, pp. 2269–2274.
Ritz, J. et al. (1980) "A monoclonal antibody to human acute lymphoblastic leukaemia antigen" *Nature*, vol. 283, pp. 583–585.
Civin, C.I. et al. (1984) "Antigenic Analysis of Hematopoiesis III. A Hematopoietic Progenitor Cell Surface Antigen Defined by a Monoclonal Antibody Raised against KG–1a Cells" *Journal of Immunology*, vol. 133, No. 1, pp. 157–165.
Craig, W. et al. (1993) "Expression of Thy–1 on Human Hematopoietic Progenitor Cells" *J. Ex. Med.*, vol. 177, pp. 1331–1342.

Berenson, R.J. et al. (1988) "Antigen CD34* Marrow Cells Engraft Lethally Irradiated Baboons" *J. Clin. Invest.*, vol. 81, pp. 951–955.
Terstappen, L.W. (1990) "Flow Cytomeric Analysis of Human Bone Marrow III. Neutrophil Maturation" *Leukemia*, vol. 4, No. 9, pp. 657–663.
Loken, M.R. et al. (1987) "Flow Cytometric Analysis of Human Bone Marrow II. Normal B. Lymphocyte Development" *Blood*, vol. 70, No. 5, pp. 1316–1324.
Friedmann, T. (1989) "Progress Toward Human Gene Therapy" *Science*, vol. 244, pp. 1275–1281.
Sutherland, H.J. et al. (1991) "Differential Regulation of Primative Human Hematopoietic Cells in Long–Term Cultures Maintained on Genetically Murine Stromal Cells" *Blood*, vol. 78, No. 3, pp. 666–672.
Terstappen, L.W. et al. (1991) "Sequential Generations of Hematopoietic Colonies Derived From Single Nonlineage–Committed CD34*CD38* Progenitor Cells" *Blood* 77(6):1218–1227.
Bender, J.G. et al. (1991) "Identification and Comparison of CD34–Positive Cells and Their Subpopulations From Normal Peripheral Blood and Bone Marrow Using Multicolor Flow Cytometry" *Blood*, vol. 77, No.12, pp. 2591–2596.
Terstappen, L.W. et al. (1991) "Sequential Generations of Hematopoietic Colonies Derived From Single Nonlineage–Committed CD34*CD38* Progenitor Cells" *Blood* vol. 77, No. 6, pp. 1218–1227.
Loken, M.R. et al. (1987) "Flow Cytometric Analysis of Human Bone Marrow I. Normal Erythroid Development" *Blood*, vol. 69, No. 1, pp. 255–263.
Simmons, P.J. et al. "Identification of Stromal Cell Precursors in Human Bone Marrow by a Novel Monoclonal Antibody, STRO–1" *Blood* (1991), vol. 7B, No. 1, 55–62.
Golde, D.W. (1991) "The Stem Cell" *Scientific American* vol. 265, No. 6, pp. 86–93.
No Authors Listed, "Gene Therapy in Man", *The Lancet* (1988), vol. 1, pp. 1271–1272.

*Primary Examiner*—Jeffrey Stucker
(74) *Attorney, Agent, or Firm*—Saliwanchik, Lloyd & Saliwanchick

(57) ABSTRACT

The subject invention pertains to antibodies that have binding specificity for an antigen that is expressed on a subset of human, hematopoietic mononuclear cells, including a hematopoietic stem cell population, but is not expressed on normal, mature myeloid cells. In one embodiment, a monoclonal antibody, MG1, is provided. This antibody is useful in methods of isolating cell suspensions from human blood and marrow that can be employed in bone marrow transplantation, genetic therapy, and in treating other diseases of the hematopoietic system. Cell suspensions containing MG1[+] human hematopoietic cells are also provided, as well as therapeutic methods employing the cell suspensions. The subject invention also pertains to the novel antigen recognized by the subject antibodies.

17 Claims, 11 Drawing Sheets

Lanes
1. 2 μl
2. 5 μl
3. Marker
4. 10 μl
5. 15 μl

```
File: DONOR      Title: DONOR BM 9/20/96
50000 Gated Events
MG 1.1 FITC(Log) vrs CD34 (QB) PE(Log) Quad Stats
Location: x 560 y 524
   Quad    X-mean   Y-mean   Events   % Gated
   (1)-UL    18.4    403.9     635     1.27
   (2)-UR   340.1    370.3     291     0.58
   (3)-LL    20.2      8.5   48906    97.81
   (4)-LR   292.7     30.0     168     0.34
```

LANES

1. Blank
2. ML1 Cell Lysate
3. KG1a Cell Lysate
4. K562 Cell lysate
5. MW Markers
6. HEL Cell Lysate
7. HT 29 Cell Lysate
8. MW Markers
9. Blank
10. ML1 Cell Lysate

LANES

1. ML1 Cell Lysate
2. Blank
3. MW Markers
4. HT 29 Cell Lysate
5. HEL Cell Lysate
6. MW Markers
7. K562 Cell lysate
8. KG1a Cell Lysate
9. ML1 Cell Lysate
10. Blank Lanes
1. ML-1
2. KG 1a
3. K 562
4. HEL
5. Marker
6. HT-29
7. Blank
8. ML-1

Lanes
1. ML-1
2. RBCs
3. Granulocytes
4. Marker
5. Lymphocytes
6. Platelets
7. ML-1

Lanes

1. O & N-Glycosidase
2. N-Glycosidase
3. O-Glycosidase
4. Control
5. Marker

LANES
1. Stained Markers
2. Unstained Markers
3. ML1 Cell Lysate
4. ML1 Cell Lysate
5. Flow Through
6. Eluate
7. Conc. (10X) Eluate
8. Eluate
9. Unstained Markers
10. Stained Markers

```
                         SEQUENCE LISTING

<160> NUMBER OF SEQ ID NOS: 1

<210> SEQ ID NO 1
<211> LENGTH: 12
<212> TYPE: PRT
<213> ORGANISM: Homo sapiens
<220> FEATURE:
<221> NAME/KEY: UNSURE
<222> LOCATION: 9
<223> OTHER INFORMATION: Unknown

<400> SEQUENCE: 1

Arg Arg Arg Ala Lys Gln Asn Gln Xaa Gly Glu Ile
  1               5                  10
```

ANTIBODY RECOGNIZING A SMALL SUBSET OF HUMAN HEMATOPOIETIC CELLS

CROSS-REFERENCE TO RELATED APPLICATIONS

This application is a division of U.S. application Ser. No. 09/873,835, filed Jun. 4, 2001, now U.S. Pat. No. 6,482,598, which is a division of U.S. application Ser. No. 09/531,827, filed Mar. 21, 2000, now U.S. Pat. No. 6,242,579, which is a division of U.S. application Ser. No. 08/970,032, filed Nov. 13, 1997, now U.S. Pat. No. 6,043,348, which claims the benefit of provisional application U.S. Ser. No. 60/030,428, filed Nov. 13, 1996.

FIELD OF THE INVENTION

The present invention relates to a novel monoclonal antibody recognizing a small subset of human hematopoietic cells, which may include the hematopoietic stem cell population.

BACKGROUND OF THE INVENTION

Hematopoietic stem cells are defined as those cells that are capable of both self-renewal and differentiation into the two principle precursor components—the myeloid and lymphoid lines. Such stem cells are said to be "totipotent." Stem cells that are less general but that can still differentiate into several lines are called "pluripotent." Further differentiation then occurs among the precursor cells to produce the monocyte, eosinophil, neutrophil, basophil, megakaryocytes, and erythroid lineages from the myeloid line, and T cells, B cells, and NK cells from the lymphoid line. For a background review of the stem cell see *Scientific American* 256:86–93 (December 1991).

One of the first breakthroughs into stem cell isolation and identification came in the late 1980's. In U.S. Pat. No. 4,714,680 (Dec. 22, 1987), Civin described a population of pluripotent lympho-hematopoietic cells that were substantially free of mature lymphoid and myeloid cells. Civin also described an antigen, MY-10, and a monoclonal antibody thereto, which was present on those cells. Those cells made up about 1% of all cells in normal adult bone marrow, and generally comprised a mixture of totipotent, and pluripotent stem cells and lineage committed precursor cells with the latter cells predominating.

Since that time, MY-10 has been classified by the International Workshop on Human Leukocyte Antigens as falling with the cluster designated as "CD34." Anti-CD34 monoclonal antibodies are now commercially available from a number of sources including, for example, Becton Dickinson Immunocytometry Systems ("BDIS").

Anti-CD34 monoclonal antibodies have been used for a number of purposes. Loken, Terstappen and their collaborators have published a series of papers describing the maturational stages for various components of the hematopoietic system, such as B lymphocytes (Loken et al., *Blood* 70:1316–1324 (November 1987)), erythroid cells (Loken et al., *Blood* 69:255–263 (January 1987)), and neutrophils (Terstappen et al., *Leukemia* 4:657–663 (September 1990)). The objective of these studies was to define, starting from the most mature cell and working backwards, the various maturational and developmental stages of a lineage committed cell.

Anti-CD34 monoclonal antibodies have also been used to look for earlier non-lineage committed stem cells. For example, Terstappen et al., *Blood* 77:1218–1227 (March 1991), described a subset of human progenitor cells that were capable of self-renewal and differentiation into each of the various hematopoietic lineages (i.e., a population of cells that include cells that are totipotent). This population was characterized as being $CD34^+/CD38^-$.

U.S. Pat. No. 5,061,620 to Tsukamoto et al. (Oct. 29, 1991) also described a population of cells that were capable of self-renewal and differentiation. This population of cells was characterized as being $CD34^+/CD10^-/CD19^-/CD33^-$ and $Thy-1^+$.

Other investigators have attempted to subset $CD34^+$ cells from both peripheral blood and bone marrow. Bender et al., *Blood* 77:2591–2596 (June 1991), used four color flow cytometry with combinations of monoclonal antibodies (i.e., anti-CD34, anti-CD33, anti-CD45, anti-CD19, anti-CD7, anti-CD 10, anti-CD3, anti-CD20, anti-CD14, anti-CD11b and anti-HLA-DR), to identify and isolate $CD34^+$ hematopoietic progenitor cells. Bender et al. were able to identify a number of subsets. One subset was $CD34^+/HLA-DR-$. This subset had a very small number of cells and no clear population of this phenotype was resolved. Bender et al. speculated on the ability of this population of cells to give rise to blast cell colonies or cells reconstituting long term cultures based upon prior work of others.

Sutherland et al., *Blood* 78:666–672 (August 1991), reported on the differential regulation of "primitive" hematopoietic cells in long term culture. They used anti-CD34 and anti-HLA-DR monoclonal antibodies to select cells that were $CD34^+$ and $HLA-DR^{dim}$ or $HLA-DR^-$. These cells were then grown on a unique stromal cell line. The purpose of this work was to establish a method of long term culture of such cells for the purposes of studying hematopoiesis and the effect of different growth factors on hematopoiesis.

Simmons et al., *Blood* 78:55–62 (July 1991), also reported on the "identification" of a stromal cell precursor in human bone marrow. Using an antibody they designated "Stro-1," Simmons et al. were able to remove stromal cells from bone marrow. The antigen recognized by this antibody was not present on colony forming progenitor cells but was present on a "subpopulation of cells experiencing the [CD34] antigen." Thus, Simmons et al. described the ability of the antibody to separate out stromal cells from hematopoietic cells in bone marrow before culture.

Verfaillie et al., *J. Exp. Med.* 172:509–520 (August 1990), reported on a $CD34^+/HLA-DR^+$ and $CD34^+/HLA-DR^-$ population of "primitive" progenitor cells. Taking adult marrow, Verfaillie et al. depleted bone marrow of lineage$^+$ cells using multiple monoclonal antibodies. Next, fluorescently labeled CD34 and HLA-DR monoclonal antibodies were used to select $HLA-DR^+$ and $HLA-DR^-$ populations that were also $CD34^+$. Having isolated these two groups, Verfaillie et al. reported that the $HLA-DR^+$ cells were better in short term culture than the $HLA-DR^-$ cells. In long term culture, the reverse was true.

WO 93/25216, published Dec. 23, 1993, teaches a population of human primitive stem cells that are capable of self-renewal and that are capable of differentiating into hematopoietic stem cells and stromal stem cells that give rise to the hematopoietic microenvironment. This population of cells has the phenotype $CD34^+/CD38/HLA-DR$. This population of cells lacks lineage committed antigens (i.e., is CD33-, CD10-, CD5-, and CD71-). Cells having this phenotype were identified in adult and fetal peripheral blood, bone marrow, thymus, liver, or spleen using a combination of antibodies and selecting for the presence or absence of the antigens recognized by these antibodies on the cells. Preferably, the combination of antibodies comprised at least three monoclonal antibodies and more preferably comprised anti-CD34, anti-CD38 and anti-HLA-DR monoclonal antibodies.

WO 94/02157, published Feb. 3, 1994, teaches the isolation of human hematopoietic stem cells that are CD34$^+$, HLA-DR and express the receptor for the c-kit ligand (KR$^+$). This cell population was reportedly useful for transplantation and in gene therapy protocols.

To date, the CD34 antigen, as identified by monoclonal antibodies, has been the only known cell surface marker to be used to define the hematopoietic stem cell compartment and has become the marker of choice not only for the identification of stem cells but also for their isolation. Published information now indicates the existence of monoclonal antibodies that define cell surface markers distinct from CD34; (i) monoclonal antibody AC 133 which binds to a surface protein of 96 kDa on approximately 50% of CD34$^+$ cells; (ii) monoclonal antibody BB9 which binds to a surface protein of 160 kDa on approximately 10–28% of CD34$^+$ cells; and (iii) a non-designated monoclonal antibody that binds to a glycoprotein 105 on the surface of hematopoietic stem cells. Virtually all of the CFU-S and colony forming unit cells detectable by in vitro stem cell assays express the CD34 antigen. Furthermore, a number of animal and human studies have demonstrated that purified CD34$^+$ cells are capable of reconstituting the entire hematopoietic system, suggesting that early engraftment by progenitor cells and long-term maintenance by primitive stem cells are mediated by this population (See, e.g., Berenson et al., *J. Clin. Invest.* 81:951–955 (1988)).

The identification and isolation of the most primitive population of hematopoietic stem cells would be highly advantageous in situations where reinfusion of only a small number of long-term repopulating cells was desired. For example, this would be the case when purging bone marrow or peripheral blood stem cells of contaminating tumor cells, or where genetic manipulation of the stem cells was the objective. CD34 expression seems to be stage specific rather than lineage specific with higher levels of expression seen in primitive progenitors and decreasing expression levels with cellular maturation (Holyoake & Alcorn, *Blood Rev.* 8(2):113–124 (1994)). Nonetheless, it has never been successfully demonstrated that stem cells could be purified on the basis of their CD34 expression levels. The studies described above suggest that CD34$^+$ cells selected for the absence of lineage specific markers, such as, CD33, CD38, HLA-DR, as well as low Thy-1 labeling (Thy$^{lo}$) (Craig et al., *J. Exp. Med.* 177:1331–1342 (1993)), correspond to a stem cell-enriched population. No positive enrichment procedure, however, has ever been described.

Clearly, there is a continuing need in the art to isolate novel markers of primitive stem cell populations so that positively enriched primitive stem cell populations can be obtained and utilized as therapeutic compositions, as well as in therapeutic methods such as bone marrow transplantation and gene therapy.

Bone marrow transplantation is an effective therapy for an increasing number of diseases. Graft Versus Host Disease (GVHD), however, limits bone marrow transplantation to recipients with HLA-matched sibling donors. Even then, approximately half of the allogenic bone marrow transplantation recipients develop GVHD. Current therapy for GVHD is imperfect and the disease can be disfiguring and/or lethal. Thus, risk of GVHD restricts the use of bone marrow transplantation to patients with otherwise fatal diseases, such as malignancies, severe aplastic anemia, and congenital immunodeficiency states.

The potential benefits from expanded use of bone marrow transplantation have stimulated research on the cause and prevention of GVHD. It has been shown that donor T lymphocytes cause GVHD in animals. Removal of T lymphocytes from donor marrow inocula ("grafts") prevented the subsequent development of GVHD in mice, dogs, and monkeys. Similar trials in humans with monoclonal antibodies against human T lymphocytes are now in progress. Preliminary results, however, suggest only attenuation of GVHD, not a cure. Similar results have been achieved with E-rosette and soybean lectin depletion of T lymphocytes. Another approach under investigation is the use of anti-T lymphocyte monoclonal antibodies conjugated to toxins, such as ricin.

As of yet, however, GVHD has not been prevented or cured in bone marrow recipients. Therefore, a continuing need exists for improved methods of combating Graft Versus Host Disease.

Donors of bone marrow are also faced with undesirable procedures and risks. The current procedures for harvesting bone marrow are expensive and painful. Furthermore, the current donation procedure is accompanied by the risks associated with anesthesia, analgesia, blood transfusion and possible infection. It would be desirable, therefore, to improve the current method of harvesting hematopoietic stem cells from donors.

BRIEF SUMMARY OF THE INVENTION

The present invention concerns an antibody that recognizes a small subset of human hematopoietic mononuclear cells, which may include the hematopoietic stem cell population. An exemplified embodiment of an antibody of the invention is the MG1 monoclonal antibody.

The MG1 antibody recognizes an antigen on a small subset of human hematopoietic mononuclear cells, but does not bind to antigens on normal, human mature myeloid cells. The invention also concerns the hybridoma which produce the MG1 antibody.

The present invention also concerns a method for preparing a cell population useful for stem cell transplantation that is positively enriched in immature marrow cells and substantially free of mature myeloid and lymphoid cells.

The present invention also pertains to a method of collecting donations useful for stem cell transplantation that avoids the disadvantages of conventional marrow harvesting techniques.

The present invention also concerns a therapeutic materials and methods for transplanting stem cells that can extend the use of stem cell transplantation to the treatment of non-fatal diseases.

The present invention also provides a method of stem cell gene therapy, utilizing antibodies of the present invention.

The present invention also pertains to materials and methods to reduce or eliminate GVHD associated with bone marrow transplantation.

In one embodiment, the present invention provides a method of selecting a population of human cells containing MG1$^+$ hematopoietic cells comprising: (a) providing a cell suspension from human tissue, such as marrow or blood; (b) contacting said cell suspension with an antibody that binds the MG1 antigen; and (c) separating and recovering from said cell suspension the cells bound by said antibody.

In a further embodiment, the present invention provides a method of selecting a population of human cells containing MG1+ hematopoietic cells comprising: (a) providing a cell suspension from human tissue, said tissue selected from the group consisting of marrow and blood; (b) contacting said cell suspension with a solid-phase linked MG1 monoclonal antibody; (c) separating unbound cells from solid-phase linked monoclonal antibody after said contacting; and (d) recovering bound cells from said solid-phase linked monoclonal antibody after separating said unbound cells.

Yet another embodiment of the present invention provides a suspension of human cells comprising MG1+ hematopoietic cells substantially free of mature cells, as well as therapeutic methods employing such a cell suspension.

In a further embodiment, the present invention provides a method of gene therapy utilizing the monoclonal antibody of the present invention to select for hematopoietic cells that express the MG1 antigen.

BRIEF DESCRIPTION OF THE DRAWINGS

The designation "Miki," appearing in any of the Figures submitted herein, and described below, is simply the former designation for "MG1," and thus, should be considered the same as MG1.

FIG. 4 shows that MG1 recognizes only a very small population (less than 1%) of cells within bone marrow, and that less than 3% of CD34+ cells co-express MG1 antigen, suggesting a very small overlap of the two populations. Quad, quadrant; UL, upper left; LR, lower right.

BRIEF DESCRIPTION OF THE SEQUENCE

Figure 1:
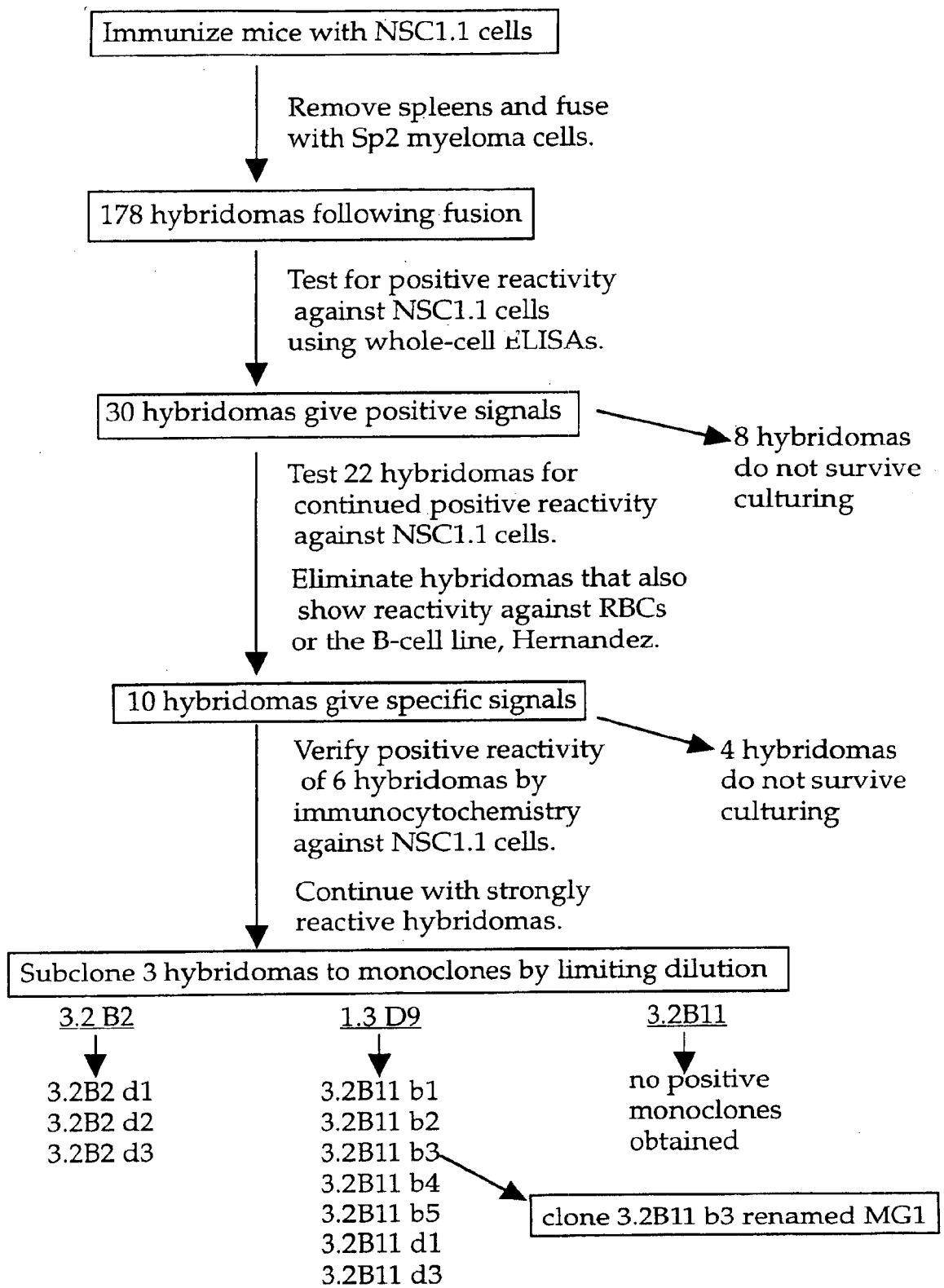
FIG. 1 is a flow chart describing the origin of the MG1 hybridoma clone.

SEQ ID NO. 1 shows a partial amino acid sequence of the MG1 antigen polypeptide according to the subject invention.

DETAILED DESCRIPTION OF THE INVENTION

The subject invention concerns a novel polypeptide antigen. The antigen, which is referred to herein as the "MG1 antigen," or alternatively, the "MG1 ligand," is expressed on a very small population of human hematopoietic cells, which may include pluripotent hematopoietic stem cells. Stem cells have the ability to restore, when transplanted, the production of myeloid and lymphoid cells to a patient who has lost such production due to, for example, radiation therapy or disease. The antigen disclosed herein is not expressed by mature myeloid cells. The newly discovered antigen may help to define a population of hematopoietic cells desirable for use in a bone marrow transplant. This antigen was identified by a monoclonal antibody raised against the human NSC1.1 cell line, which is derived from the ML-1 cell line.

The present invention also concerns antibody that can bind to the MG1 antigen. An exemplified embodiment of the invention is a monoclonal antibody, referred to herein as "MG1," that facilitates the isolation of the desired cells and makes possible improved therapeutic techniques that significantly contribute to the understanding and prevention of Graft Versus Host Disease. The isolated stem cells can also be employed to produce panels of monoclonal antibodies to stem cells. The monoclonal antibodies of the invention can also be employed in stem cell gene therapy.

The ML-1 cell line used as an immunogen as described herein was derived from an enriched, immunoselected, $CD34^+$ population isolated from normal human cadaveric bone marrow (U.S. Pat. No. 5,650,299, issued Jul. 22, 1997). The immunoselected $CD34^+$ cells were cultured, in vitro, in the presence of either recombinant IL-3, and IL-6, or native, semi-purified stem cell proliferation factor (SCPF). SCPF is a cytokine that promotes the proliferation of primitive hematopoietic stem cells while maintaining their CD34 phenotype. The cells were grown in the presence of these exogenous cytokines for a period of several months. CD34 cells grown in the presence of IL-3 and IL-6 differentiated and the cultures were lost. However, the culture supplemented with SCPF were SCPF-dependent and continued to proliferate. The SCPF-dependency was lost over time and the cell cultures became SCPF-independent. This population of cells was examined by flow cytometry and was shown to express CD34. This cell line was designated ML-1. The ML-1 cell line was cloned by limiting dilution and rescreened by flow cytometry and a sub clone of ML-1 was established that was phenotypically more primitive than that of the parental cell line. This cell line was designated NSC1.1. Given the primitive nature of this cell population, this clone of ML-1 was used as the immunogen for the hybridoma program.

The MG1-ligand is expressed as a cell-surface antigen on the NSC1.1 cell line. The antigen can be immunoprecipitated from extracts of this cell line as a glycosylated protein of approximately 186±5% kD (kilodalton) apparent molecular weight.

Antibodies that specifically label a subset of hematopoietic progenitors are extremely useful in hematopoietic research because they allow the isolation of relatively pure populations of immature hematopoietic cells in a single step. Cells recovered with MG1 antibody could be an appropriate normal cell population to compare with leukemic blast cells and to use in studies on the mechanisms of action of cells, factors, and genes that regulate hematopoietic cell proliferation and differentiation.

MG1 antibody did not recognize cells from three human leukemic cell lines (e.g., KG-1a, K562, HEL 92.1.7), and did not bind to human peripheral blood cells. MG1 did not bind to mouse bone marrow cells.

Monoclonal anti-stem cell antibodies can be produced readily by one skilled in the art. The general methodology for making monoclonal antibodies using hybridoma technology is now well known in the art. See, e.g., M. Schreier et al., *Hybridoma Techniques* (Cold Spring Harbor Laboratory 1980); Hammerling et al., *Monoclonal Antibodies and T-Cell Hybridomas* (Elsevier Biomedical Press 1981); Kennett et al., *Monoclonal Antibodies* (Plenum Press 1980). Immortal, antibody-secreting cell lines can also be produced by techniques other than fusion, such as direct transformation of B-lymphocytes with oncogenic DNA or EBV. Several antigen sources can be used, if desired, to challenge the normal B-lymphocyte population that is later converted to an immortal cell line.

For example, the NSC1.1 cell line can be used as an immunogen to challenge the mammal (e.g., mouse, rat, hamster, etc.) used as a source for normal B-lymphocytes. The antigen-stimulated B-lymphocytes are then harvested and fused to an immortal cell line or transformed into an immortal cell line by any appropriate technique. A preferred hybridoma producing the monoclonal MG1 antibody is produced by challenging a mouse with the NSC1.1 cell line and fusing the recovered B-lymphocytes with an immortal SP2/0-Ag14 myeloma cell. Antibody-producing immortal cells can be screened for anti-stem cell antibody production by selecting clones that are strongly reactive with the NSC1.1 cells, but not reactive with granulocytes from a panel of human donors. Antibodies produced by clones which show those properties can then be screened for the additional properties of anti-stem cell antibodies.

A mouse hybridoma producing monoclonal MG1 antibody was deposited with the American Type Culture Collection (ATCC), 10801 University Blvd., Manassas, Va. 20110-2209, on Nov. 6, 1996, and assigned ATCC Accession No. HB12232.

The subject cell line has been deposited under conditions that assure that access to the culture will be available during the pendency of this patent application to one determined by the Commissioner of Patents and Trademarks to be entitled thereto under 37 CFR 1.14 and 35 USC 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject cell line deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the cell line. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

In a preferred embodiment, the present invention encompasses any monoclonal antibody that recognizes the MG1 antigen, i.e., the antigen recognized by antibody from the hybridoma ATCC HB12232. In another preferred embodiment, the present invention contemplates monoclonal antibodies that correspond to the monoclonal antibody produced by ATCC HB12232, and, in a particularly preferred embodiment, the ATCC HB12232 antibody. One antibody corresponds to another antibody if they both recognize the same or overlapping antigen binding sites as demonstrated by, for example, a binding inhibition assay.

An alternative to the above method of producing monoclonal antibodies employs the MG1 antigen directly as an immunogen. The monoclonal antibody produced by hybridoma ATCC HB12232 can be readily employed to purify the MG1 antigen. In one example of immunopurification, MG1 antigen can be immunoprecipitated from cell extracts of the NSC1.1 cell line. The precipitated antigen can be used as an immunogen in place of the NSC1.1 cell line in the above method. By application of any of the above methods, one skilled in the art can readily produce a panel of monoclonal antibodies, screen them with partially purified MG1, and obtain anti-MG1-ligand antibodies.

Another alternative is to use an MG1 antibody in the production of monoclonal antibodies that recognize different antigens on MG1$^+$ cells. The cells isolated from blood and marrow with MG1 antibody can be used as an immunogen, as described above, to produce a panel of monoclonal antibodies against MG1$^+$ cells. The production of such antibodies is greatly facilitated by the use of substantially pure populations of hematopoietic cells provided by the MG1 antibody. The specificities of such antibodies can be determined readily through routine screening by one skilled in the art. Thus, additional stage-specific, lineage independent antigens (and antibodies to these antigens) can be identified by those skilled in the art.

MG1 recognizes a marker on the surface of hematopoietic cells that is distinct from CD34. Consequently, use of the MG1 antibody provides an alternative (or additional) means for the positive selection of a subset of this population from human bone marrow or peripheral blood. Given that MG1$^+$ cell populations represent only a subset of the CD34 population, antibodies immunoreactive with the MG1 antigen can be used in the field of tumor cell purging of bone marrow or peripheral blood stem cells, as well as in the preparation of stem cell populations for genetic therapy.

The antibodies according to the subject invention may be either monoclonal, polyclonal, or a mixture of monoclonal and/or polyclonal antibodies. The antibody may comprise whole antibody or antigen-binding fragments thereof, such as $Fab_2$, Fab and Fv fragments. Antigen binding fragments can be prepared using conventional techniques known in the art, such as proteolytic digestion of antibody by papain or pepsin, or through standard genetic engineering techniques known in the art. Monoclonal antibodies exemplified herein can be engineered so as to change the isotype of the antibody. For example, the MG1 antibody, which is an $IgG_{2A}$ isotype, can be engineered as an $IgG_1$, $IgG_{2B}$, or other isotypes. Also contemplated by the subject invention are antibodies that are reactive with the MG1 antibody and which have been engineered to comprise human antibody constant regions. "Humanized" antibodies can be prepared using standard methods known in the art. See, for example, U.S. Pat. No. 5,585,089 (issued Dec. 17, 1996), the disclosure of which is hereby incorporated by reference.

The antibodies of the subject invention can be labeled according to standard methods known in the art. For example, antibodies can be labeled with detectable labels such as fluorescein, rhodamine and radioactive isotopes.

As indicated above, one application for monoclonal antibodies to lineage independent antigens on stem cells is the isolation of a highly enriched source of stem cells for human bone marrow transplantation. Such sources of stem cells can prevent or attenuate Graft Versus Host Disease. Anti-stem cell monoclonal antibodies can also be used to isolate stem cells for autologous reinfusion, for example, in the treatment of antigen-negative leukemias or other malignancies.

The present invention contemplates the use of any method employing the MG1 monoclonal antibody to separate stem cells from mature lymphocytes in the marrow or blood. Generally, a cell suspension prepared from human tissue containing cells (i.e., marrow or blood cells) is brought into contact with the MG1 monoclonal antibody. Cells that have been bound by the monoclonal antibody are then separated from unbound cells by any means known to those skilled in the art.

Various methods of separating antibody-bound cells from unbound cells are known. For example, the antibody bound to the cell (or an anti-isotype antibody) can be labeled and then the cells separated by a mechanical cell sorter that detects the presence of the label. Fluorescence-activated cell sorters are well known in the art. In one preferred embodiment, the anti-stem cell antibody is attached to a solid support. Various solid supports are known to those of skill in the art, including, but not limited to, agarose beads, polystyrene beads, hollow fiber membranes, polymers, and plastic petri dishes. Cells that are bound by the antibody can be removed from the cell suspension by simply physically separating the solid support from the cell suspension. Preferred protocols, however, will be described.

Selective cytophoresis can be used to produce a cell suspension from human bone marrow or blood containing pluripotent hematopoietic stem cells. For example, marrow can be harvested from a donor (the patient in the case of an autologous transplant; a donor in the case of an allogeneic transplant) by any appropriate means. The marrow can be processed as desired, depending mainly upon the use intended for the recovered cells. The suspension of marrow cells is allowed to physically contact, for example, a solid phase-linked monoclonal antibody that recognizes an antigen on the desired cells. The solid phase-linking can comprise, for instance, adsorbing the antibodies to a plastic, nitrocellulose, or other surface. The antibodies can also be adsorbed on to the walls of the large pores (sufficiently large to permit flow-through of cells) of a hollow fiber membrane. Alternatively, the antibodies can be covalently linked to a surface or bead, such as Pharmacia Sepharose 6 MB macrobeads. The exact conditions and duration of incubation for the solid phase-linked antibodies with the marrow cell suspension will depend upon several factors specific to the system employed. The selection of appropriate conditions, however, is well within the skill of the art.

The unbound cells are then eluted or washed away with physiologic buffer after allowing sufficient time for the stem cells to be bound. The unbound marrow cells can be recovered and used for other purposes or discarded after appropriate testing has been done to ensure that the desired separation had been achieved. The bound cells are then separated from the solid phase by any appropriate method, depending mainly upon the nature of the solid phase and the antibody. For example, bound cells can be eluted from a plastic petri dish by vigorous agitation. Alternatively, bound cells can be eluted by enzymatically "nicking" or digesting a enzyme-sensitive "spacer" sequence between the solid phase and the antibody. Spacers bound to agarose beads are commercially available from, for example, Pharmacia.

The eluted, enriched fraction of cells may then be washed with a buffer by centrifugation and either cryopreserved in a viable state for later use according to conventional technology or immediately infused intravenously into the transplant recipient.

In a particularly preferred embodiment, stem cells can be recovered directly from blood using essentially the above methodology. For example, blood can be withdrawn directly from the circulatory system of a donor and percolated continuously through a device (e.g., a column) containing the solid phase-linked monoclonal antibody to stem cells and the stem cell-depleted blood can be returned immediately to the donor's circulatory system using, for example, a conventional hemapheresis machine. When a sufficient volume of blood has been processed to allow the desired number of stem cells to bind to the column, the patient is disconnected from the machine. Such a method is extremely desirable because it allows rare peripheral blood stem cells to be harvested from a very large volume of blood, sparing the donor the expense and pain of harvesting bone marrow and the associated risks of anesthesia, analgesia, blood transfusion, and infection.

The above cell populations containing MG1$^+$ enriched human hematopoietic cells can be used in therapeutic methods such as stem cell transplantation, as well as other methods that are readily apparent to those skilled in the art. For example, such cell populations can be intravenously administered to a patient requiring a bone marrow transplant in an amount sufficient to reconstitute the patient's hematopoietic and immune system. Precise, effective quantities can be readily determined by those skilled in the art and will depend, of course, upon the exact condition being treated by the therapy. In many applications, however, an amount containing approximately the same number of stem cells found in one-half to one liter of aspirated marrow should be adequate.

In another embodiment, the MG1 monoclonal antibody can be used to isolate MG1$^+$ cells, which can be used in various protocols of genetic therapy.

The optimal choice of target tissue for gene therapy is a long-lived, preferably self-renewing cell. The hematopoietic stem cell is particularly attractive as a target for gene therapy for several reasons. First, the procedures for the collection, cryopreservation, and reinfusion of human bone marrow are well developed, and the efficacy well established. Second, the use of stem cells or very early pluripotential precursor cells would assure long term maintenance of the genetically modified cells, and thus reduce the number of interventions required. Third, one of the obstacles faced by gene therapists is that sustained high level expression of transgenes has been difficult to achieve in large outbred mammals (Blaese, R. M., *Clinical Immunology and Immunopathology*, (61):547–555 (1991); Miller, A. D., *Nature* 357:455–460 (1992)). One of the ways to address this problem has been to use expression systems adapted to the target tissue (Kay et al., *Hum. Gene Ther*, 3:641–647 (1992)). In the hematopoietic system, precursor (stem) cells can differentiate along one of three developmental pathways that produce large numbers of terminally differentiated cells, myeloid, lymphoid and erythroid cells. The control of gene expression during the development of the hematopoietic system has been extensively studied (Evans et al., *Ann. Rev. Cell Biol*, 6:95–124 (1990)), and elements implicated in the tissue-specific expression of genes have been identified for all three developmental pathways. The therapeutic transgene could be genetically modified to be constitutively expressed or expressed specifically in one of the differentiated hematopoietic lineages. Fourth, small numbers of hematopoietic stem cells produce very large numbers of differentiated cells; this diminishes the burden on the transducing procedure to be of very high efficiency or throughput since a small population of genetically modified stem cells will generate a large population of genetically modified cells within the patient. Finally, since small numbers of genetically modified cells are necessary, the risk associated with the introduction of large numbers of genetically modified cells into patients is also diminished.

The use of a stem cell-specific antibody need not be limited to the purification of stem cells prior to a transfection procedure. With the goal of generating vectors for in vivo gene therapy, it has been proposed to engineer into the gene therapy vectors themselves, mechanisms by which the vector will recognize its target cell (and preferably only its target) within the context of the entire organism. See, Kasahara et al., *Science* 266:1373–1376 (1994); Michael & Curiel, *Gene Therapy* 1:223–232 (1994); Chatterjee et al., *Ann. N.Y. Acad. Sci*, 770:79–90 (1995); Schwarzenberger et al., *Blood* 87:472–478 (1996). By incorporating stem cell-specific antibodies into a vector, it may be possible to generate vectors that will recognize and target hematopoietic stem cells in the patient's bone marrow. Specifically, the antibody could be incorporated into liposome vectors, (Hughes et al., *Cancer Res*, 49:6214–6220 (1989); Wang & Huang, *Biochemistry* 28:9508–9514 (1989); Ahmad et al., *Cancer Res*, 53:1484–1488 (1993)), poly-L lysine conjugate vectors (Michael & Curiel, supra; Schwarzenberger et al., supra), or into viral vectors, including but not limited to adenoviral vectors, retroviral vectors, (Russell et al., *Nucleic Acids Res*, 21:1081–1085 (1993); Somia et al., *Proc. Natl. Acad. Sci. USA* 92:7570–7574 (1995)), and adeno-associated vectors (Chattejee et al., supra), modified to express on the vector surface, the antibody itself or proteins which would bind the antibody to the vector surface (such as the Fc receptor).

These vectors, although partly conceived for use in in vivo gene therapy can also be used to target the same $MG1^+$ cells in ex vivo applications, on either pre-selected $MG1^+$ cells, or on whole bone marrow, mobilized peripheral blood stem cells, or cord blood stem cells.

In a preferred method of in vivo gene therapy, genetic disorders, such as, e.g., sickle cell anemia, β-thalassemia, Fanconi anemia, and other hemoglobinopathies, may be corrected by the introduction of the normal gene into a human stem cell, which can then be transplanted into a patient's bone marrow. The treatment of genetic disease using genetically modified stem cells is not limited to the treatment of hematopoietic tissues and diseases, but can also be extended to diseases in which the presence of a circulating protein is of clinical benefit, such as Gaucher disease and hemophilia A and B.

To effect gene therapy with a substantially pure population of human progenitor cells, the following method may be used to insert a gene into these cells. For a general review of the methodologies, see Friedmann, T., *Science* 244:1275–1281 (June 1989) and *Lancet* 1:1271–1272 (Jun. 4, 1988).

A therapeutic gene can be introduced into the population of purified stem cells, isolated as above by; (1) physical methods such as coprecipitation with calcium phosphate, electroporation or microinjection (e.g., U.S. Pat. No. 4,873, 191), and/or (2) the use of viral vectors such as adenoviral, or retroviral vectors. In the latter case, the DNA of the retrovirus is cut with a restriction enzyme and the human DNA containing the desired sequence is inserted and ligated. The retrovirus containing the insertion is then infected into the stem cells. The stem cells can then be assayed for production of the desired protein. See, e.g., U.S. Pat. No. 4,902,783.

In general, molecular DNA cloning methods are well known in the art and are not limiting in the practice of this invention. For a further description of similar methods, see Friedmann, T., *Science* 244:1275–1281 (1989) and *Molecular Cloning: A Laboratory Manual,* 2nd ed., J. Sambrook et al., eds., Cold Spring Harbor Laboratory Press, Cold Spring Harbor, N.Y. (1989).

To transplant the stem cells containing the desired gene, the cells may be introduced into the bone marrow of the patient by conventional means of bone marrow transfer. Typically, this involves the intravenous delivery of the cells over a period of time. The bone marrow of the patient may be lethally irradiated prior to infusion to assure that the transplanted stem cells fully replace the existing bone marrow cells. See U.S. Pat. No. 4,721,096 to Naughton et al. (Jan. 26, 1988).

In another method of gene therapy, drug resistance genes (i.e., dihydrofolate reductase (dhfr), MDR1) can be introduced into normal stem cells and then transplanted into a cancer patient undergoing chemotherapy to protect the healthy stem cells from the toxic effects of the drug. This procedure would allow more aggressive chemotherapeutic regimens to be employed. (Guigon et al., *Bone Marrow Transplant* 13:93–95 (1994); Baum et al., *J. Virol,* 69:7541–7547 (1995)). $MG1^+$ cell populations maybe useful in this method. Modified stem cells also have applications in the treatment of certain acquired diseases such as HIV infections (Nienhuis et al, *Cancer* 67(10 Suppl.):2700–2704 (1991); Bahner et al., *J. Virol.* 70:4352–4360 (1996)).

In another method of gene therapy, the MG1 antibody can be used in an antibody modified delivery system to target drug delivery specifically to $MG1^+$ hematopoietic cells in vivo. See, e.g., Ahmad et al., *Cancer Res*, 53:1484–1488 (1993).

The subject invention also pertains to the gene encoding the MG1 antigen polypeptide. Contemplated within the scope of the invention are natural and allelic variant polynucleotide sequences encoding the MG1 antigen, as well as degenerate polynucleotide sequences that encode the MG1 antigen polypeptide. Polynucleotide sequences encoding the MG1 antigen can be readily obtained using materials of the subject invention and standard methods known in the art. For example, a cDNA library can be prepared from NSC1.1 cells and that cDNA library inserted into an appropriate expression system, such as lambda phage. Clones can then be screened for expression products using, for example, an MG1 antibody. Clones that are positive for expression of a polypeptide that binds to MG1 antibody can be further evaluated by sequencing of the cDNA insert, Western blot, etc.

Polynucleotide sequences encoding the MG1 antigen can also be obtained using degenerate oligonucleotide probes based on the amino acid sequence of the MG1 antigen in conjunction with standard RACE procedures known in the art. For example, 5' RACE can be performed using a MARATHON cDNA amplification kit (CLONTECH Laboratories, Palo Alto, Calif.) to amplify a 5' RACE fragment from $polyA^+$ RNA obtained from cells that express the MG1 antigen. The RACE fragments generated using the degenerate oligonucleotide probes can then be cloned and characterized by sequencing. Full length cDNA sequences can then be generated by end to end PCR or by conventional cloning methods known in the art.

Other methods for screening for polynucleotide sequences encoding the MG1 antigen are known in the art. These include, for example, screening DNA libraries using degenerate oligonucleotide probes that can be prepared based on the partial amino acid sequence of the MG1 antigen. Also contemplated within the scope of the present invention are fragments and variants of the polynucleotide encoding MG1 antigen, as well as fragments and variants of the MG1 antigen itself. The fragments of the subject polynucleotides can be readily prepared using standard methods known in the art. For example, digestion using the BAL31 exonuclease can be used to prepare 5' and 3' nucleotide deletions.

The subject invention also pertains to anti-idiotypic antibodies that possess binding specificity for idiotypic determinants associated with anti-MG1 antigen antibodies of the present invention. The anti-idiotypic antibodies that the invention can be prepared using the anti-MG1 antigen antibodies as an immunogen according to standard methods for producing anti-idiotypic antibodies known in the art. Also included within the scope of the present invention are antigen binding fragments of whole anti-idiotypic antibody, wherein the fragments retain substantial by the same binding specificity as the whole antibody molecule. The antigen binding fragments include, for example, Fab$_2$, Fab and Fv fragments.

The subject invention also concerns kits comprising a compartment containing at least one anti-MG1 antigen antibody, anti-idiotypic antibody or an MG1 antigen. In one embodiment, the anti-MG1 antigen antibody is the MG1 antibody disclosed herein.

Antibodies to the MG1 antigen can also be used to investigate differential expression of the MG1 antigen on tumor cells versus normal cells. Thus, the subject invention also concerns methods for identifying tumor cells, such as leukemic cells, from normal cells by contacting a sample with an antibody of the invention and determining whether the antibody binds to any of the test cells. In a preferred embodiment, MG1 antigen expression on cells is determined using the MG1 antibody of the present invention.

The subject invention also concerns methods for treating tumors in patients using an antibody of the subject invention that binds to an MG1 antigen. In a preferred embodiment, the method comprises administering an effective amount of an MG1 antigen binding antibody to a patient in need of such treatment. Methods for administering antibodies to treat various disease states are known in the art. Preferably, the antibody is modified in a manner so as to minimize any immune response to the antibody when it is administered to the patient. For example, the antibody can be "humanized," such as by replacing non-human constant regions of the antibody with human constant regions, according to methods known in the art. A variety of toxic agents capable of killing or inhibiting the replication of a cell can be conjugated to the antibody. For example, a variety of cytotoxic agents are available in the art. These include, for example, radionuclides (Iodine-131, Yttrium-90 and the like), chemotherapeutic agents (such as methotrexate, cisplatinum and the like) and cytotoxic proteins (such as ricin, exotoxins, diphtheria toxins and the like). In one embodiment, the method can be used to treat leukemia.

The following examples are provided to illustrate specific embodiments of the present invention. The examples are included for illustrative purposes only, and are not intended to limit the scope of the present invention.

Materials and Methods

Preparation of Cell Line for Use as an Immunogen

NSC1.1 cells were grown in T-75 cm$^2$ tissue culture flasks using the following growth medium: Iscove's modified Dulbecco's medium (IMDM) supplemented with 10% fetal bovine serum (FBS), L glutamine (0.292 mg/ml) and antibiotics (50 Units/ml penicillin, and 50 Units/ml streptomycin). Once the NSC1.1 cells reached confluency, the supernatants were harvested, centrifuged (2000 rpm for 4 minutes at room temp.), and the cell pellet resuspended in IMDM growth medium (as stated above). The concentration of viable cells at time of harvest was estimated (using trypan blue dye exclusion) and the cell suspension adjusted to a concentration of 1.5×10$^8$ cells/ml. The cells were then washed four times in sterile phosphate buffered saline (PBS) at pH 7.5 and finally resuspended in one ml of PBS at a concentration of 1.5×10$^8$/ml.

Mice Immunization Protocol

Three 23–27 day-old female Balb/c mice (Charles River Laboratories, MD) were injected with 200 µl of the NSC1.1 cell suspension (3×10$^7$ total cells) via the intra-peritoneal (I/P) route. As a control, one mouse was injected, I/P, with 200 µl of PBS only. Following the initial injection, the mice were immunized in the manner and over the time course set out below:

| Time | Protocol | Route Inoculum |
|---|---|---|
| Day 0 (Jan. 23, 1995) | Primary Immun. | I/P 3 × 10$^7$ Ml-1 cells |
| Day 15 (Feb. 7, 1995) | First Booster | I/P 3 × 10$^7$ Ml-1 cells |
| Day 23 (Feb. 17, 1995) | Second Booster | I/P 3 × 10$^7$ Ml-1 cells |
| Day 33 (Feb. 27, 1995 | Final Booster[I] | I/V[ii] 10$^7$ Ml-1 cells |
| Day 36 (Mar. 2, 1996) | Harvest spleen for fusion & hybridoma production | |

Notes:
[I]Blood was collected (tail vein bleed) from all experimental mice on day 33. The sera from these bleeds was removed and the level of the anti NSC1.1 response was measured by both flow cytometry and immunocytochemistry (see attached methods).
[ii]I/V = Intravenous injection Established Cell Lines Used Sp2/0-Ag14: Sp2/0-Ag14 (ATCC CRL-1581) is a non-secreting myeloma hybrid of murine origin that is routinely used in the fusion process of hybridoma production.

KG1a: KG1a (ATCC CCL-246.1) is a variant subline of the human, acute myelogenous leukemia cell line KG1 (ATCC CCL-246). KG1a was the cell line that was used to manufacture the MY10 monoclonal antibody that defines the CD34 antigen. See U.S. Pat. No. 4,965,204 (Oct. 25, 1990) to Civin.

K562: K562 (ATCC CCL-243) is a continuous cell line established from a human with chronic myelogenous leukemia. The cell line is characterized as a highly undifferentiated blast of the granulocytic series. Recent studies indicate that the K562 cells are undifferentiated blasts that are multipotential and capable of differentiating into progenitors of the erythrocytic, granulocytic, and monocytic series.

HT-29: HT-29 (ATCC HTB-38) is a human colon adenocarcinoma.

HEL 92.1.7: Hel 92.1.7 (ATCC TIB-180) is a lymphoblastic-like cell line derived from an erythroleukemia. This cell line is capable of both spontaneous and induced globin synthesis.

Hybridoma Production

Prior to the fusion, Sp2/0-Ag14 myeloma cells were tested for their sensitivity to Hypoxanthine, Aminopterin, Thymidine (HAT) containing medium. The Sp2/0-Ag14 myeloma cells are hypoxanthine-guanine phosphoribosyl-transferase (HGPRT) negative and, therefore, are sensitive to the presence of HAT whereas normal spleen cells are HGPRT$^+$ and are resistant to HAT. The HGPRT mutation was, therefore, used in the positive selection of hybrid cells (spleen/myeloma).

HAT-sensitive Sp2/0-Ag14 cells were harvested, from culture, centrifuged (2000 rpm, 4 minutes), and the pellets resuspended in IMDM supplemented with L glutamine (0.292 mg/ml) and antibiotics (50 Units/ml penicillin, and 50 Units/ml streptomycin). Cell counts were performed by trypan blue dye exclusion.

The 3 experimental mice (immunized with NSC1.1 cells as described above) were sacrificed by cervical dislocation and their spleens removed using aseptic techniques. The spleens were kept separate and placed in 100 mm petri dishes containing 10 ml of the IMDM supplemented with L glutamine (0.292 mg/ml) and antibiotics (50 Units/ml penicillin, and 50 Units/ml streptomycin). Cell suspensions from each spleen were made in the above medium, washed twice and viable cells enumerated, by trypan blue dye exclusion. The Sp2/0-Ag14 myeloma cell and spleen cell suspension were mixed together at a ratio of 1:5 (myeloma:spleen) in the presence of polyethylene glycol (PEG) 1500 (Boehringer Mannheim).

The fusion mixture was then incubated at 37° C. for 10 minutes. Following the incubation step, the cell-fusion mixture was centrifuged and resuspended in 30 ml of fresh IMDM supplemented with 20% fetal bovine serum (FBS), L glutamine (0.292 mg/ml) and antibiotics (50 Units/ml penicillin, and 50 Units/ml streptomycin). The myeloma/ spleen cell fusion mixture, for each mouse, was added in 100 $\mu$l volumes ($5\times10^5$ spleen cells/well) to each well of three 96-well microplates. The microplates (a total of 9 plates) were then incubated at 37° C. in a humidified atmosphere of 5% $CO_2$ in air. Four hours after incubation at 37° C., 100 $\mu$l of IMDM containing 20% fetal bovine serum (FBS), L glutamine (0.292 mg/ml) and antibiotics (50 Units/ml penicillin, and 50 Units/ml streptomycin) and further supplemented with 2×HAT was added to each well of the nine 96-well microplates.

All the microplates were then re-incubated at 37° C. in a humidified atmosphere of 5% $CO_2$ in air and checked daily for the appearance of hybridoma growth. Every third day, 100 $\mu$l of supernatant from each of the wells was removed and replenished with fresh IMDM growth media plus HAT. The media removed from the individual wells was then used to screen for positive NSC1.1 reactivity. Screening was carried out using a sandwich ELISA and/or immunocytochemistry.

The multi-clone wells that were identified as having NSC1.1 specific immunoglobulins in the supernatant, by either test, were grown to high cell density and subsequently passaged into new wells of a 96-well microplate. These multi-clones were routinely screened for reactivity with the immunizing NSC1.1 cell line. If the clone(s) maintained their reactivity they were expanded to tissue culture containers with greater surface area. Excess cells from each positive clone were stored in liquid nitrogen. Once positive clones were established, the antibody reactivity was tested (ELISA, flow cytometry, and/or immunocytochemistry) against a wider variety of targets, which included cell lines, KG1a, K562, HT-29, and HEL 92.1.7, described above, and peripheral blood leukocytes (granulocytes, lymphocytes, monocytes, and thrombocytes). All clones with unique antibody profiles were then subjected to limiting dilution cloning to produce a monoclonal hybridoma secreting an antibody of a single isotype and with a defined antigen specificity.

Detection of Antibody-Positive Clones by a Sandwich-Enzyme Linked Immunoadsorbent Assay (ELISA)

The sandwich ELISA technique used was modified from the method as described by Harlow & Lane, "Chapter 14: Immunoassays," in Antibodies: A Laboratory Manual, Harlow & Lane, eds., Cold Spring Harbor Laboratory Press, Cold Spring Harbor, N.Y. (1988), pp. 553–612. Briefly, the ELISA was run in U-shaped, 96-well microplates whose wells had been previously blocked, overnight, with 3% bovine serum albumin (BSA) in PBS, (pH 7.5). Cells to be used as the antigen (NSC1.1, KG1a, K562, HT29, and HEL92.1.7) were washed three times in PBS, resuspended in PBS, enumerated (by trypan blue dye exclusion) and the cell number adjusted to $2\times10^6$/ml. One hundred microliters ($2\times10^5$ cells/well) of these cell suspensions were then added to each well of 96-well plates. All the plates containing the cells were subjected to centrifugation (2000 rpm, for 5 minutes at 4° C.) and the supernatants from each of the wells aspirated. Cells were resuspended in 100 $\mu$l of undiluted test hybridoma supernatant and incubated at 28° C. (room temperature) for 60 minutes. Each test hybridoma was run in triplicate wells. Following incubation with the hybridoma supernatant, the cells were centrifuged (2000 rpm, 4° C., for 4 minutes) washed once with PBS and the cell pellets resuspended in 50 $\mu$l of biotinylated rabbit/goat anti-mouse immunoglobulin (Ig) (Vectastain Elite ABC Kit, Vecta Labs, Burligame, Calif.). The plates were then re-incubated at 28° C. for a further 60 minutes. The cells were again washed once in PBS and then resuspended in 100 $\mu$l of Vectastain ABC Avidin-HRP conjugate with a final incubation of 30 minutes at 28° C. After incubation, the cells were washed once with PBS and the pellet resuspended in 100 $\mu$l of substrate-2,2 Azino-bis-3 ethylbenz-thiazoline-6 sulphonic acid (ABT) (Sigma Chemicals Co, St. Louis, Mo.). The reaction was allowed to proceed for ten minutes, after which the reaction was stopped. The assay was read spectrophotometrically at 405 nm and the data recorded. Results were determined to be positive if the O.D. reading was 2 standard deviations above the negative control.

Detection of Antibody-Positive Clones by Immunocytochemistry

The immunocytochemical procedure was as described in the manufacturer's instructions for the use of the Vectastain ABC Elite Kit (Vecta Labs, Burligame, Calif.). Briefly, cells to be used (NSC1.1, KG1a, K562, HT29, HEL 92.1.7) were centrifuged (2000 rpm, 4° C., for 4 minutes) and the cells resuspended in PBS. The cells were washed a further 5 times in PBS and finally resuspended, in PBS, enumerated (Trypan blue dye exclusion) and the cell concentration adjusted to $1\times10^6$/ml. Two hundred microliters of each cell suspension were added to the cytospin chambers of a cytocentrifuge and were then centrifuged onto glass slides (500 rpm for 5 minutes). Once the cells were deposited onto the glass microscope slides, they were air-dried then fixed in methanol at room temperature. Prior to testing hybridoma supernatants, the endogenous peroxide activity was quenched by incubating the cell smears with a 1% solution of hydrogen peroxide ($H_2O_2$) solution for one hour at room temperature. The slides were washed of excess $H_2O_2$ and then incubated for 60 minutes at room temperature with the undiluted test hybridoma supernatants. Following this step, the excess supernatant was removed, the slides rinsed in 3×250 ml beakers containing fresh PBS, and each of the cell smears incubated at room temperature for 30 minutes with 50 $\mu$l biotinylated rabbit/goat anti-mouse Ig. Following the second antibody step, the slides were again washed in PBS, as stated above, and incubated at room temperature for 30 minutes with 50 $\mu$l of Avidin-HRP conjugate, washed, then incubated for ten minutes with 100 $\mu$l of the substrate 3,3 diaminobenzidine (DAB). The reaction was stopped, air dried and the cells permanently fixed and mounted under Dpex and a glass coverslip. All slides were then examined by light microscopy (using either 40× objective or 40× oil objective). The results were scored as follows:

| | |
|---|---|
| ++++ | Very strong positive reaction |
| +++ | Strong positive reaction |
| ++ | Positive reaction |
| + | Weak positive reaction |
| − | Negative reaction |

Detection of Antibody Positive Clones by Flow Cytometry

For the detection of binding of specific antibody to the surface of NSC1.1 cells, flow cytometry was carried out as described below. Briefly, staining of the NSC1.1 cells was performed on two-to-three day old cell cultures. Cells were adjusted to a cell concentration of 1×10⁶ cells per sample (200 µl) in IMDM containing 1% fetal bovine serum (FBS), L glutamine (0.292 mg/ml) and antibiotics (50 Units/ml penicillin, and 50 Units/ml streptomycin). To the cells was added 100 µl of the test hybridoma supernatant, the mixture vortexed, and incubated for 30 minutes on ice. Following incubation, the samples were washed in the above media and the cells resuspended in 200 µl of IMDM medium (shown above) and 50 µl of fluorescein isothiocyanate (FITC)-labeled goat anti-mouse IgG (Fab)'2 (GAM-FITC). The labeled cells were then incubated for 30 minutes on ice. After labeling, the cells were again washed, resuspended in 1 ml of the above IMDM medium and then subjected to flow analysis using an Epics Elite ESP (Coulter Corporation, Hialeah, Fla.) equipped with a 488 nm argon air-cooled laser. Forward and side scatter gates were adjusted to include live cells only. Results of the analysis were based on the collection of 10,000 data points per sample.

Separation of Peripheral Blood Leukocyte Sub-Sets by Self Generated PERCOLL Gradients Subsets of peripheral blood leukocytes were separated using PERCOLL (Pharmacia, Piscataway, N.J.) according to the method described in the manufacturer's instructions. The self generating 70% PERCOLL (in 0.15M NaCl) gradients were generated by centrifuging 10 ml of PERCOLL solution in 15 ml pyrex glass tubes (Coming, Cambridge Mass.), at 20,000×g (J20 rotor) for 15 minutes at 110° C. Two ml of fresh citrated (an anticoagulant) peripheral blood was then overlaid onto the PERCOLL gradients and centrifuged at 800×g for 25 minutes at 10° C. Following centrifugation, the blood cells were separated according to their densities, i.e., platelets remained at the blood/PERCOLL interface, mononuclear cells (lymphocytes and monocytes) banded in the center of the gradient, and the polymophonuclear cells (granulocytes) and erythrocytes banded to the bottom of the gradients. Using a 5 ml pipette the layers of discrete cells were harvested from the gradient, placed in separate 15 ml polypropylene tubes, centrifuged (2000 rpm for 4 minutes at room temperature) and the pellets washed 3 times in IMDM (without supplements). The final cell pellet was then resuspended in IMDM (without supplements) at the required cell concentrations for either immuno-staining or western blot analysis.

Characterization of the Monoclonal Antibody Isotype

The identification of the monoclonal antibody isotype(s), being secreted by hybridomas of interest, was carried out using a mouse Ig typing kit (Pharmingen, San Diego, Calif.). The procedure was as described in the manufacturer's instructions for use. Briefly, 100 µl of rat monoclonals, with specificity for each mouse Ig isotype was aliquoted in wells (8 wells/isotype) of a flat-bottomed microplate and incubated at 4° C. overnight. Following the overnight incubation, the supernatants from each well were aspirated, 300 µl of a 3% BSA solution (blocking agent) was added, and the plates incubated for a further 30 minutes at room temperature. Following this incubation step, the microplates were washed 5 times with PBS/TWEEN 20 (0.5%) and 100 µl of test hybridoma supernatant added after the last wash. The plates were incubated for 60 minutes at room temperature. After incubation, the plates were then washed, as previously described, and 100 µl of alkaline phosphatase labeled polyclonal rat anti-mouse Ig added, and the plates re-incubated for 60 minutes at room temperature. Prior to the substrate being added, the plates were washed 5 times in PBS/TWEEN 20. The substrate (p-N.P.) and its concentration used were as suggested in the isotyping kit. Following the color development, the results were determined using a spectrophotometer at a wave length of 405 nm.

Preparation of Cell Lysates for SDS-PAGE

Cells were harvested, centrifuged (2000 rpm at room temperature) and washed 4 times in PBS. After the final wash, the cell pellets were resuspended (vortexed) in lysis buffer (0.1% TRITON-X 100 in PBS, and 1 mM phenylmethyl-sulfonylfluoride (PMSF) and incubated on ice for 60 minutes. After incubation, the cell lysates were clarified by centrifugation (14,000 rpm at 4° C. for 45 minutes) and the supernatant collected and used as a stock cell lysate preparation.

Protein Molecular Weight Determination by Sodium Dodecyl Sulfate Polyacrylamide Gel Electrophoresis (SDS-PAGE)

The SDS-PAGE procedure used was as described by Laemmli, Nature 227:680–685 (1970). Samples (cell lysates) were prepared for one dimensional SDS-PAGE by boiling the lysate for 5 minutes in the presence of SDS and 2.5% β-mercaptoethanol. Protein samples were routinely resolved using a premade 10% polyacrylamide gel (BioRad Inc., Richmond, Calif.). Gels were run at a constant voltage of 75V for approximately 4–5 hours. Pre-stained SDS-PAGE molecular weight standards (BioRad Inc., Richmond, Calif.) were routinely included on each gel. Electrophoresed gels were stained either using Coomassie blue-R250 (Sigma Chemicals, St. Louis, Mo.) or by silver stain (BioRad Inc., Richmond, Calif.). The approximate molecular weight of proteins of interest was calculated using regression analysis.

Detection of Antibody Ligands by Western Blot Analysis

Western blot analysis using the ECL detection system (Amersham, Arlington Heights, Ill.) was carried out as described by Boman et al., Nature 358:512–514 (1992); Dalemans et al., Nature 354:526–528 (1991); Egan et al., Nature 358:581–584 (1992); and Kleijmeer et al., Nature 357:342–344 (1992). Cell associated proteins were separated using SDS-PAGE, as previously described. These SDS-PAGE gels were then electroblotted onto pre-blocked nitrocellulose membranes (BioRad Inc., Richmond, Calif.). The blocking of nitrocellulose membranes was accomplished by overnight treatment at 4° C. of the membranes with 5% non fat dry skimmed milk powder dissolved in PBS plus 0.01% TWEEN 20. The electroblot and transfer of the proteins to the nitrocellulose was performed using a Tris-Glycine transfer buffer containing 0.1% SDS and was carried out for 90 minutes at a constant voltage (100V). Following transfer, the nitrocellulose membranes were washed in a wash buffer (PBS, pH 7.5, plus 0.01% TWEEN 20) and then incubated at room temperature for 60 minutes with primary antibody (¹⁄₁₀ dilution of hybridoma supernatant in 25 ml of blocking solution or 14 µg of purified antibody in blocking solution). Following the incubation with the primary antibody the membranes were washed in PBS/0.01% TWEEN 20 and the horseradish peroxidase labeled goat anti-mouse IgG secondary antibody was added (¹⁄₂₀₀₀ dilution). The membranes were re-incubated at room temperature for 30 minutes then washed three times in PBS. Detection of antigen/antibody complexes was performed using the chemiluminescent reagent from Amersham's ECL system. The resulting X-ray films were developed using a Kodak M35A X-OMAT processor and the autroradiographs examined for positive reactions.

Determination of Protein Glycosylation

The presence/absence of carbohydrate moieties on the MG1 antigen was assessed by enzyme deglycosylation of the protein backbone. In this assay, digestion of any sugar present results in a shift in molecular weight that can be visualized by SDS-PAGE and western blot analysis. Deglycosylation of the MG1 antigen was carried out using the following enzymes: for O-linked sugar determination, O-glycosidase (Boehringer Mannheim, Indianapolis, Ind.), for N-linked sugar determination, N-glycosidase (Boehringer Mannheim, Indianapolis, Ind.). Briefly, NSC1.1 lysate (50 µg total protein) was aliquoted into 1.5 ml microfuge tubes and to these tubes was added either N-glycosidase (6 Units/50 µg protein), O-glycosidase (25 mUnits/50 µg protein) or a combination of the two. A microfuge tube containing 50 µg of protein only (no enzymes) was used as an untreated control. All of the tubes were incubated for 24 hours in a 37° C. waterbath. Following incubation, 100 µl of 2×SDS reducing sample buffer was added to all tubes, and then placed in a boiling waterbath for 5 minutes. The samples were run on a SDS-PAGE (as previously described), electroblotted onto a nitrocellulose filter, and then probed using the MG1 monoclonal antibody (as described above).

Purification of Mouse Monoclonal Immunoglobulins by Affinity Chromatography

The purification of immunoglobulins from 3.2B11.b3 hybridoma supernatants, using affinity-based chromatography, was as described by Schwartz, L., "Use of immobilized protein A to purify immunoglobulins," in *Bacterial Immunoglobulin-Binding Proteins: Applications in Immunotechnology*, M. D. P. Boyle, Academic Press (1990), pp. 309–339, and Walker, W. B., "Use of imunobilized protein G to isolate IgG," in *Bacterial Immunoglobulin-Binding Proteins: Applications in Immunotechnology*, M. D. P. Boyle, Academic Press (1990), pp. 355–368. Briefly, stock cultures of the hybridoma were centrifuged (2000 rpm, for 4 minutes at room temperature), then resuspended in fresh IMDM supplemented with 5% FBS (Ultra-low IgG, Life Technologies), and placed in $T_{150}$ cm$^2$ tissue culture flasks and grown at 37° C., in a humidified atmosphere of 5% $CO_2$ in air. Once the hybridoma reached confluency, supernatants from the cultures were harvested, centrifuged (2000 rpm for 10 minutes at room temperature), and then sterilized using a 0.22 µm filter (Amicon, Beverly, Mass.). Five ml HITRAP protein G columns (Pharmacia Biotech, Piscataway, N.J.) were equilibrated with 20 ml of 20 mM sodium phosphate buffer (pH 7.0). Approximately 500 ml of hybridoma supernatant was loaded using a peristaltic pump, onto each pre-equilibrated column at the flow rate of 1 ml/min. The column was then placed in line on a Pharmacia Fast Protein Liquid Chromatography (FPLC) system and again washed with 20 mM sodium phosphate, buffer (pH 7.0) until the UV detector/chart recorder returned to baseline. The bound IgG was then eluted with 10–15 ml of 0.1M glycine buffer (pH 2.7) at a flow rate of 1 ml/minute and collected as a single fraction in a tube containing 200 µl of 1M Tris-HCL (pH 9.0).

The purified IgG fraction was desalted against 20 mM sodium-phosphate buffer (pH 7.0) using PD-10 gel filtration columns (Pharmacia Biotech, Piscataway, N.J.) as per manufacturer's instructions. Concentration of the purified IgG was carried out using a Centriplus 10 (Amicon) and centrifuged at 3000×g for 60 minutes. Protein concentration was determined by Bradford protein assay and SDS-PAGE gels were run to ascertain the purity of the immunoglobulin preparation. The antibody was then stored at 4° C. or −20° C.

Purification of MG1 antigen by Affinity Chromatography

Purification of the cell surface antigen or ligand recognized by the MG1 monoclonal antibody was carried out by immuno-affinity chromatography as previously described (Harlow & Lane, "Chapter 13: Immunoaffinity Purification," in *Antibodies: A Laboratory Manual*, Harlow & Lane, eds., Cold Spring Harbor Laboratory Press, Cold Spring Harbor, N.Y. (1988), pp. 511–552). Purified MG1 IgG was covalently coupled to the sepharose matrix of a HITRAP NHS-activated 5 ml column (Pharmacia Biotech, Piscataway, N.J.) as per manufacturer's instructions. Briefly, the column was connected to a peristaltic pump and washed with 30 ml of ice-cold 1 mM HCL at a flow rate of 2 ml/min. Twelve mg purified MG1 IgG (in 25 ml of 0.2 M $NaHCO_3$, 0.5 M NaCl, pH 8.3) was then pumped onto the column at the flow rate of 1 ml/min. The MG1 containing solution was recirculated and pumped back over the column. The column was incubated for 30 minutes at room temperature (25° C.). Excess active groups were deactivated by washing the column with 0.5 M ethanolamine, 0.5 M NaCl, pH 8.3 and non-specifically bound ligands were eluted off the column with 0.1 M acetate, 0.5 M NaCl, buffer (pH 4.0).

The MG1-immuno-affinity column was equilibrated with 30 ml of 20 mM sodium-phosphate (pH 7.0). Ten ml of NSC1.1 cell lysate (prepared as stated above) was loaded into a 10 ml FPLC superloop (Pharmacia Biotech, Piscataway, N.J.) and injected onto the column at the flow rate of 0.5 ml/min. The column was then washed with 20 mM sodium-phosphate, (pH 7.0) until no UV absorbance was recorded in the flow-through. The bound ligands were eluted with 10 ml of 0.1M glycine (pH 2.7) and collected as a single fraction in a tube containing 200 µl of 1 M Tris-HCl, (pH 9.0).

The eluted fraction containing the MG1 antigen was desalted against 20 mM sodium-phosphate buffer, (pH 7.0) using PD-10 gel filtration columns (Pharmacia Biotech, Piscataway, N.J.) as per manufacturer's instructions. Concentration of the purified MG1 antigen was carried out using a Centriplus 10 (Amicon) and centrifuged at 3000×g for 60 minutes. Purity of the MG1 antigen and its apparent molecular mass was assessed by SDS-PAGE and Western blotting.

Determination of the Amino Acid Composition of the MG1-Antigen

The amino acid composition of the MG1-antigen was determined as follows. The MG1-antigen was purified by immunoaffinity column purification, followed by SDS-PAGE and transfer of the ligand band to PVDF membranes. The amino acids were quantitatively released, without degradation, by hydrolysing 0.45 µg of the purified MG1-antigen with 6N HCl for 24 hours at 110° C. under vacuum. After hydrolysis, the sample was dried and reconstituted for analysis.

Amino acid analyses were performed on the Applied Biosystems Model 420A Analyzer, an automated PTC amino acid analysis system. Briefly, the sample was applied to a glass frit support, which delivered the sample to a flow-through reaction chamber where the amino acids were derivatized with PTC using 5% phenylisothiocyanate in heptane. After derivatization, the PTC-amino acids were transferred on-line to an HPLC where each of the PTC-amino acids is separated based on its retention on a reverse phase C18 HPLC column. Amino acid composition is determined with an overall error of approximately 10%, however, by restricting further analyses to specific amino acids that give more reliable results, it is possible to improve the accuracy. The amino acid composition data was used to attempt to identify the protein by comparison to the available protein databases using the ExPASy, (Wilkins, M. R. et al., *Bio/Technology* 14:61–65 (1996), and Wilkins, M. R et al., *Biochem. Biophys. Res. Commun*, 221:609–613 (1996)), and Propsearch (Hobohm, U., et al.,*Analytical Biochemistry* 222:202 (1994)) programs.

Detection of Laminin Reactivity by Western Blot Analysis

The reactivities of the MG1 antibody against mouse laminin, and of the MG1-antigen with anti-laminin polyclonal antibodies, were determined by western blot, essentially as described above. Briefly, NSC1.1 lysate, NSC1.1 conditioned medium, and purified mouse laminin, were run in triplicate on SDS-PAGE and transferred to nitrocellulose membranes as described. Following transfer, the nitrocellulose membranes were separated into three parts and the individual parts were washed in a wash buffer (PBS, pH 7.5, plus 0.01% TWEEN 20) and then incubated at room temperature for 60 minutes with primary antibody. The membranes were labeled with anti-laminin polyclonal antibody (rabbit serum, against human placental laminin, Chemicon International Inc.; lot # 58296268) at a 1:2000 dilution, or MG1 monoclonal antibody (1/10 dilution of hybridoma supernatant in 25 ml of blocking solution or 14 µg of purified antibody in blocking solution), or PBS alone. Following incubation with the primary antibody, the membranes were washed in PBS/0.01% TWEEN 20 and horseradish peroxidase labeled goat anti-mouse (or donkey anti-rabbit) IgG secondary antibody was added (1/2000 dilution). The membranes were re-incubated at room temperature for 30 minutes, then washed three times in PBS. Detection of antigen/antibody complexes was performed using the chemiluminescent reagent from Amersham's ECL system. The resulting X-ray films were developed using a Kodak M35A X-OMAT processor and the autroradiographs examined for positive reactions.

EXAMPLE 1

Characterization of the MG1 Monoclonal Antibody

The Derivation of the 3.2.B11.b.3 Hybridoma Subclone

The three mice immunized with the NSC1.1 subclone (NSC-1.1) were sacrificed and their spleens used in fusion experiments for hybridoma production. Use of the spleens for fusion was based upon the reactivity, as measured by both flow cytometry and immunocytochemistry, of the individual mouse sera with NSC1.1 cells. The sera from all three mice gave very strong reactions using both detection systems.

The origin of the NSC1.1-specific hybridoma subclone (3.2.B11.b3) is shown in FIG. 1. Due to bacterial contamination of the mouse#2 spleen/SP2/0 fusion culture, no clones developed. From the remaining two mice (#1 and #3), 178 hybridomas (polyclones) were recorded. Supernatants removed from all 178 hybridomas were tested utilizing an indirect ELISA. Thirty of these hybridomas gave strong positive reactions against the NSC1.1 cell line. Over a period of two weeks, the 30 hybridoma cultures were expanded and continually monitored for reactivity to the NSC1.1 cell line. During this period, eight hybridomas were lost. The ELISA screening of the remaining 22 clones was also expanded to include erythrocytes as an antigen. Clones that had significant reactivity to both NSC1.1 cells and erythrocytes were then discarded. From these experiments, only 10 hybridoma clones gave positive reactions against NSC1.1 cells alone. Following further passage of these 10 clones, 4 clones were lost. The remaining 6 clones were expanded to T75 cm² tissue culture flasks and samples from each stored in liquid nitrogen. Verification of NSC1.1 reactivity by all 6 clones was assessed by immunocytochemistry. Three clones with the strongest reactivity (3.2.B2, 3.2.B11, and 1.3.D9) were then subcloned by limiting dilution to obtain single cell hybridomas. All attempts to subclone 1.3 D9 to obtain single cell clones failed. Three monoclones were generated from the limited dilution cloning of 3.2.B2 and 7 monoclones were generated from the limited dilution cloning of 3.2.B11, one of which was 3.2.B11.b3. This clone was subsequently shown to secrete a monoclonal antibody of unique specificity and was designated "MG1."

Purification and Isotype Identification of the Monoclonal Antibody Secreted by the Hybridoma 3.2.B11.b3 (MG1)

Figure 2:
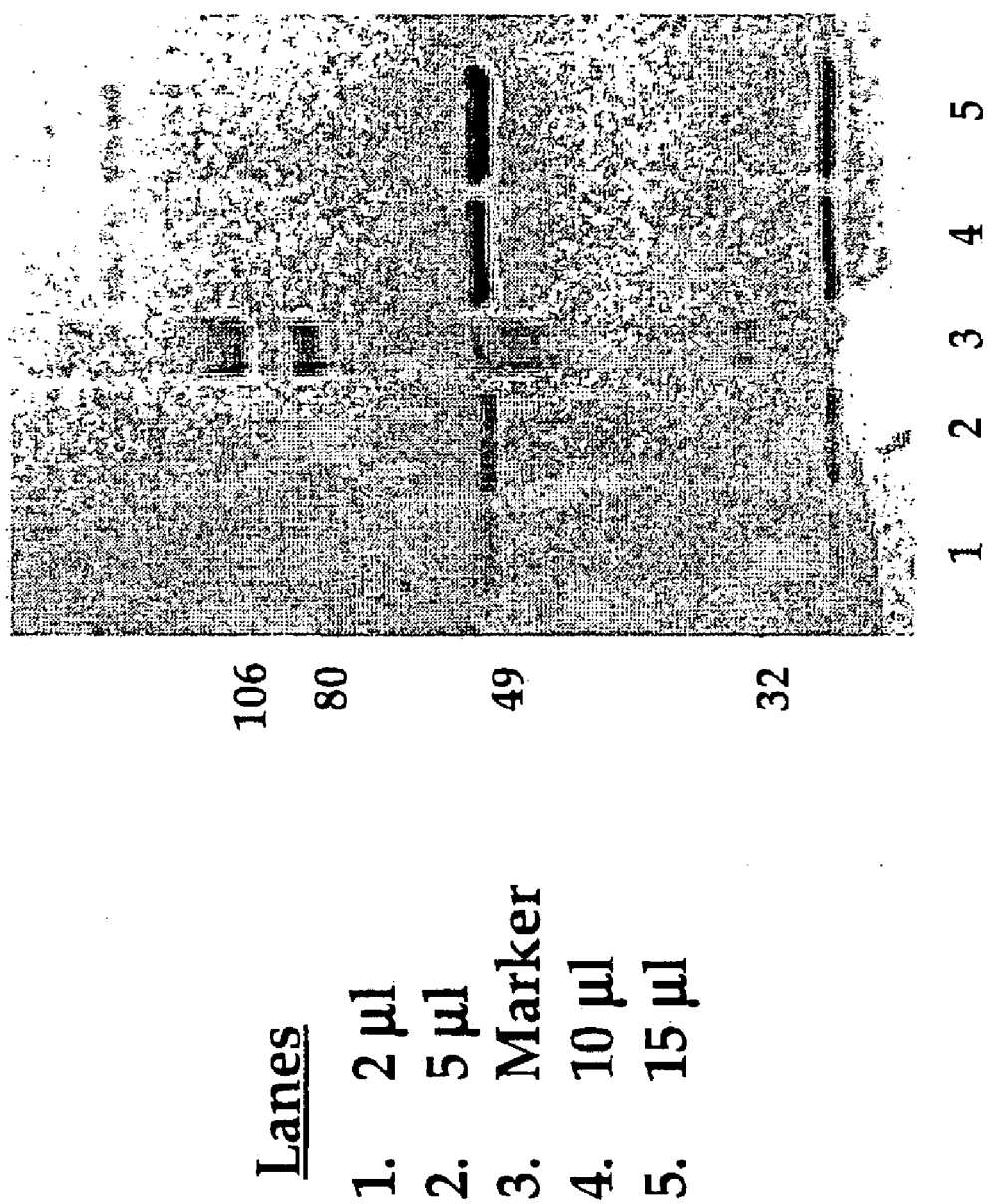
FIG. 2 shows an SDS PAGE of purified MG1 IgG. Different volumes of de-salted, purified MG1 immunoglobulin were analyzed by 10% SDS-PAGE. The gel was fixed, and stained with coomassie blue, and photographed. 2 $\mu$l, 5 $\mu$l, 10 $\mu$l and 15 $\mu$l indicate the volumes of purified MG1 immunoglobulin loaded per well. Marker: BioRad low range prestained markers: the positions of the 106, 80, 49, and 32 kDa bands are indicated.

The monoclonal antibody secreted by the 3.2.B11.b3 hybridoma was purified to homogeneity using protein-G affinity chromatography. The protein eluted from the column was subjected to SDS-PAGE electrophoresis to ascertain the purity of the preparation. The photomicrograph of a Coomasie blue-stained SDS-PAGE of the eluted protein, at different concentrations (FIG. 2), shows two distinct bands; one protein band at approximately 60 kDa (an equivalent molecular weight to the heavy chain of an Ig) and the other at approximately 28 kDa (an equivalent molecular weight to the light chain of Ig). There is no evidence of other protein(s) in the purified preparation.

Identification of the mouse immunoglobulin isotype for the MG1 antibody was carried out using the Pharmingen isotype typing kit, the results of which are shown in Table 1.

TABLE 1

| ISOTYPE OF MG1 IMMUNOGLOBULIN | | | | |
|---|---|---|---|---|
| Anti-isotype Ab | MG1 IgG | MG1 IgG | positive control | negative control |
| Anti-IgG 1 | 0.019 | 0.025 | 0.768 | 0.023 |
| Anti-IgG 2a | 0.871 | 0.808 | 0.435 | 0 000 |
| Anti-IgG 2b | 0.034 | 0.038 | 2.725 | 0.000 |
| Anti-IgG 3 | 0.029 | 0.035 | 0.208 | 0.000 |
| Anti-IgM | 0.027 | 0.076 | 1.073 | 0.000 |
| Anti-IgA | 0.026 | 0.027 | 0.597 | 0.010 |
| Anti-Ig Lκ | 2.452 | 2.373 | 1.147 | 0.004 |
| Anti-Ig Lλ | 0.020 | 0.019 | 0.807 | 0.000 |

The isotype of the purified MG1 immunoglobulin was determined by ELISA. Plates pre-coated with anti-isotype antibody were blocked with 3% BSA in PBS, before the addition of the MG1 or control immunoglobulins. Alkaline phosphatase tagged rat anti-mouse Ig was used as the secondary antibody. Reactions were read spectrophotometrically at 405 nm. Background levels of absorbance were determined for each row using wells treated with only the immobilized anti-isotype antibody, the enzyme tagged secondary antibody, and enzyme substrate. The positive control used was mouse immunoglobulin cocktail. The negative control used was mouse myeloma (Sp2/014) supernatant. The data shows that the MG1 isotype is murine IgG2a.

Figure 3:
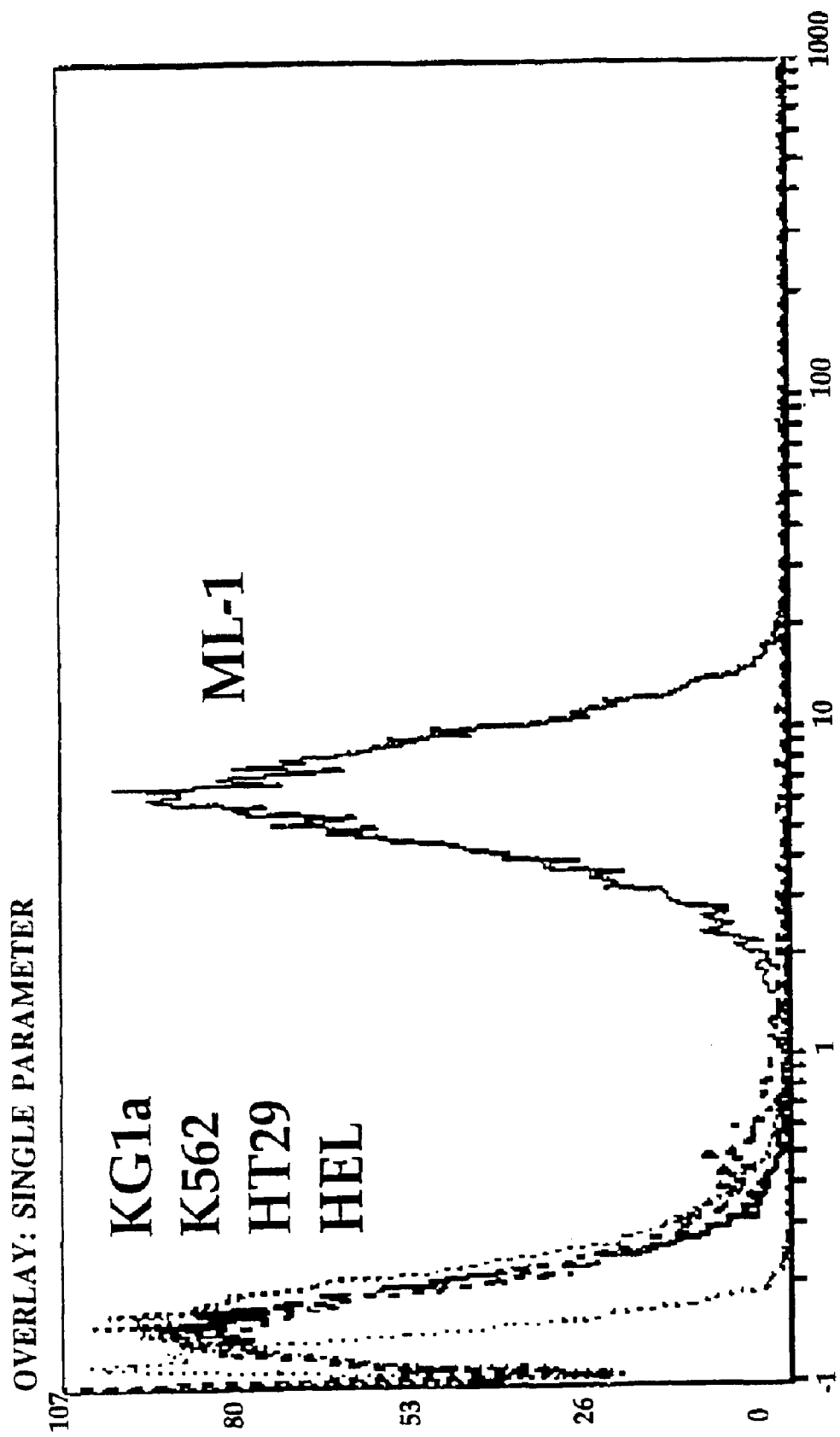
FIG. 3 shows MG1 antigen expression on the surface of various cells lines. ML-1 (NSC1.1), KG1a, K562, HT 29, and Hel cells were incubated with MG1 hybridoma supernatant, then fluorescently labeled with goat anti-mouse FITC-labeled polyclonal antibody, and examined for the presence of surface labeling by flow cytometry.

The Reactivity of Clone 3.2.B11.b3 (MG1) with Established Cell Lines Derived from Hematopoietic Malignancies, HT-29 Cells, and Normal Human Bone Marrow Given the fact that the NSC1.1 cell line was derived from a human hematopoietic stem cell population (CD34+), it was likely that the MG1 antibody would recognize stem cells and/or immature (progenitor) cells of the hematopoietic system. To test this, flow cytometry was performed on tumor cell lines isolated from malignancies of early stem cells, namely KG1a (an acute myelogenous leukemia), K562 (a chronic myelogenous leukemia), and HEL 92.1.7 (an erythroleukemia), and on normal human bone marrow. From the flow cytometric analysis data (FIG. 3), it is evident that the MG1 monoclonal antibody, while recognizing 96.9% of NSC1.1 cells, does not recognize any of the cells representing these three leukemias. It is interesting to note that KG1a was the cell line used to discover the CD34 antigen and since MG1 does not recognize KG1a, it is highly probable that MG1 does not recognize the CD34 antigen. Further, the MG1 monoclonal antibody did not label HT-29 cells. This non-hematopoietic cell line is derived from a human colon adenocarcinoma. These results suggest that MG1 is not recognizing antigens present on non-hematopoietic tissues.

Figure 4:
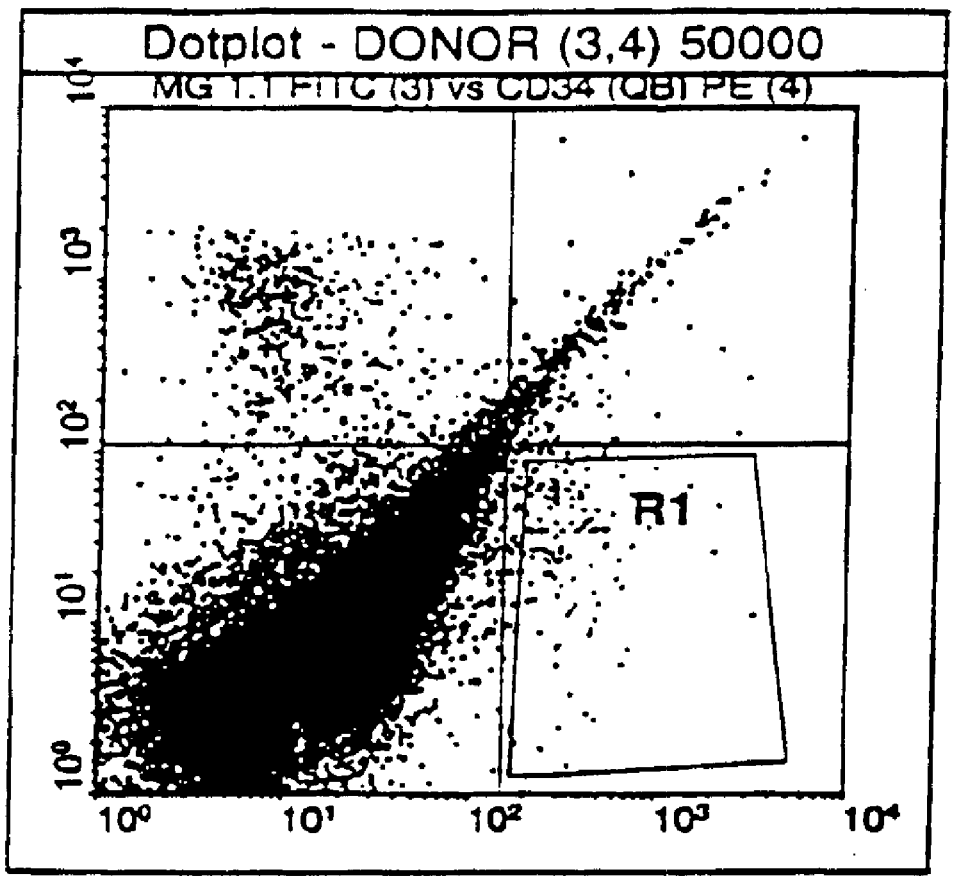
FIG. 4 shows a flow cytometry analysis of whole human bone marrow using fluorescein-labeled MG1 monoclonal antibody. Whole normal adult human bone marrow was labeled with MG1-FITC and anti-CD34-PE (QBend 10), fixed, and analyzed by flow cytometry. 50,000 events were collected. The x-axis depicts MG1-associated fluorescence intensity. The y-axis depicts CD34-associated fluorescence intensity. MG1 positive cells (lower right quadrant) represent less than 1% of all bone marrow cells, whereas, CD34+ cells (upper left quadrant) represent approximately 1% of all bone marrow cells.

Using fluorescein-labeled MG1 monoclonal antibody, whole human bone marrow was analyzed by flow cytometry. The data from FIG. 4 gives further evidence that MG1 recognizes only a very small population (less than 1%) of cells within bone marrow. Furthermore, live-gating on $CD34^+$ cells indicated that less than 3% of $CD34^+$ cells co-express MG1 antigen, suggesting a very small overlap of the two populations.

Utilizing immunomagnetic bead cell separation technology and purified MG1 antibody, $MG1^+$ bone marrow cells were recovered. When the colony-forming potential of the $MG1^+$-selected and the MG1-depleted populations were compared in CFU-GEMM assays, it was observed that the $MG1^+$ cells were nearly 300-fold poorer at forming colonies than the MG1-depleted population (0.23 colonies per $10^5$ cells vs. 70±17 colonies per $10^5$ cells, respectively. The lack of CFU activity exhibited by the MG1 cells with recombinant human IL-3, IL-6, and Epo in CFU-GEMM assays gave further evidence to the primitive nature of the $MG1^+$ cell population. It is well established that quiescent hematopoietic stem cells, while retaining high proliferating potential, fail to respond to exogenous cytokines in CFU assays. (Berardi et al., *Science* 267:104–108 (1995)). These cells however, will respond and proliferate in ex vivo long term culture initiating cell (LTCIC) assays. Berardi et al., *Science* 267:104–108 (1995); Id.; Young et al., *Blood* 87:545–556 (1996).

Analysis of Specificity of the MG1 Monoclonal Antibody by Western Blot

Figure 5:
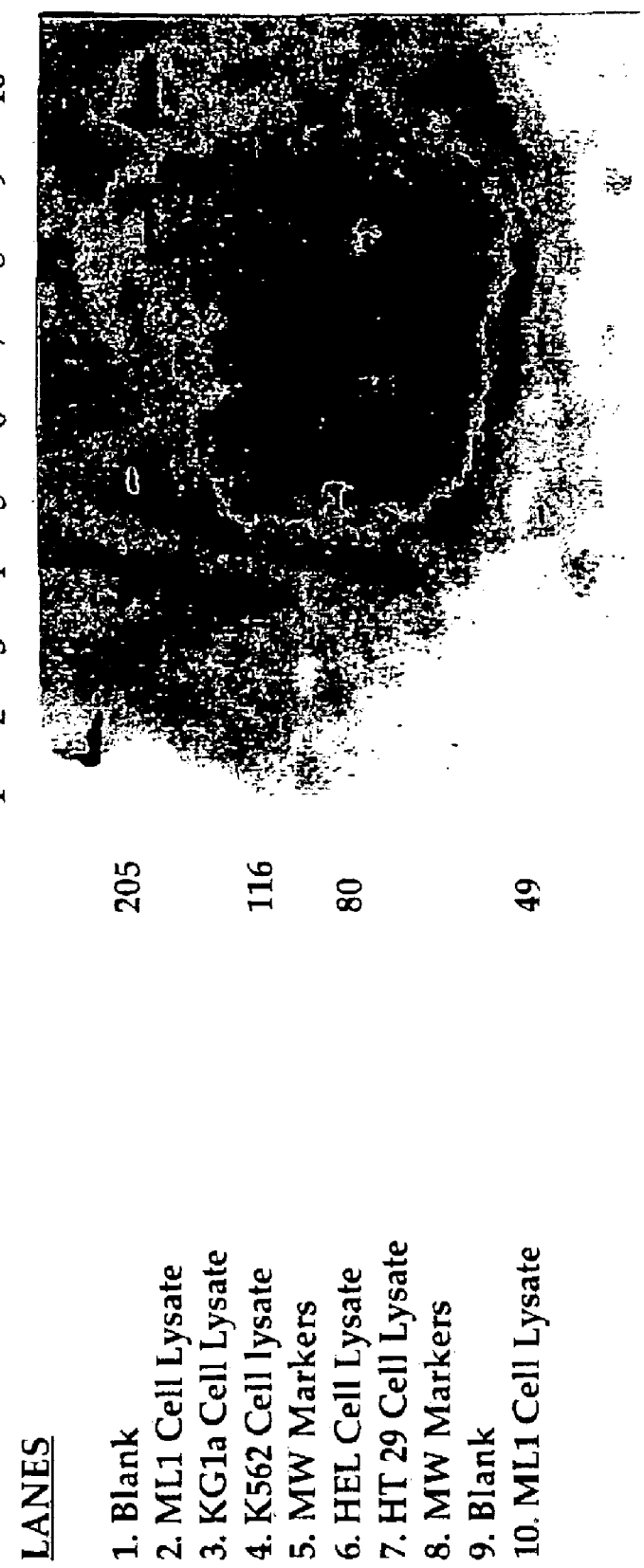
FIG. 5 shows hybridization of Western blot with MG1 antibody showing the approximate molecular weight of the MG1 antigen. Cell extracts from $10^6$ cells, prepared from various cell lines, were separated by SDS PAGE through 10% gels, and transferred to nitrocellulose membranes. The membrane was probed with MG1 primary antibody (hybridoma supernatant at a 1:100 dilution), and HRP-conjugated sheep anti-mouse IgG secondary antibody, and visualized by ECL. Marker: BioRad high range prestained markers; the positions of the 205, 116, and 80 kDa bands are indicated with short lines. ML-1; NSC1.1 cell extracts. HT-29, HEL, K562, and KG1a, refer to cell extracts from the respective cell lines.
Figure 6:
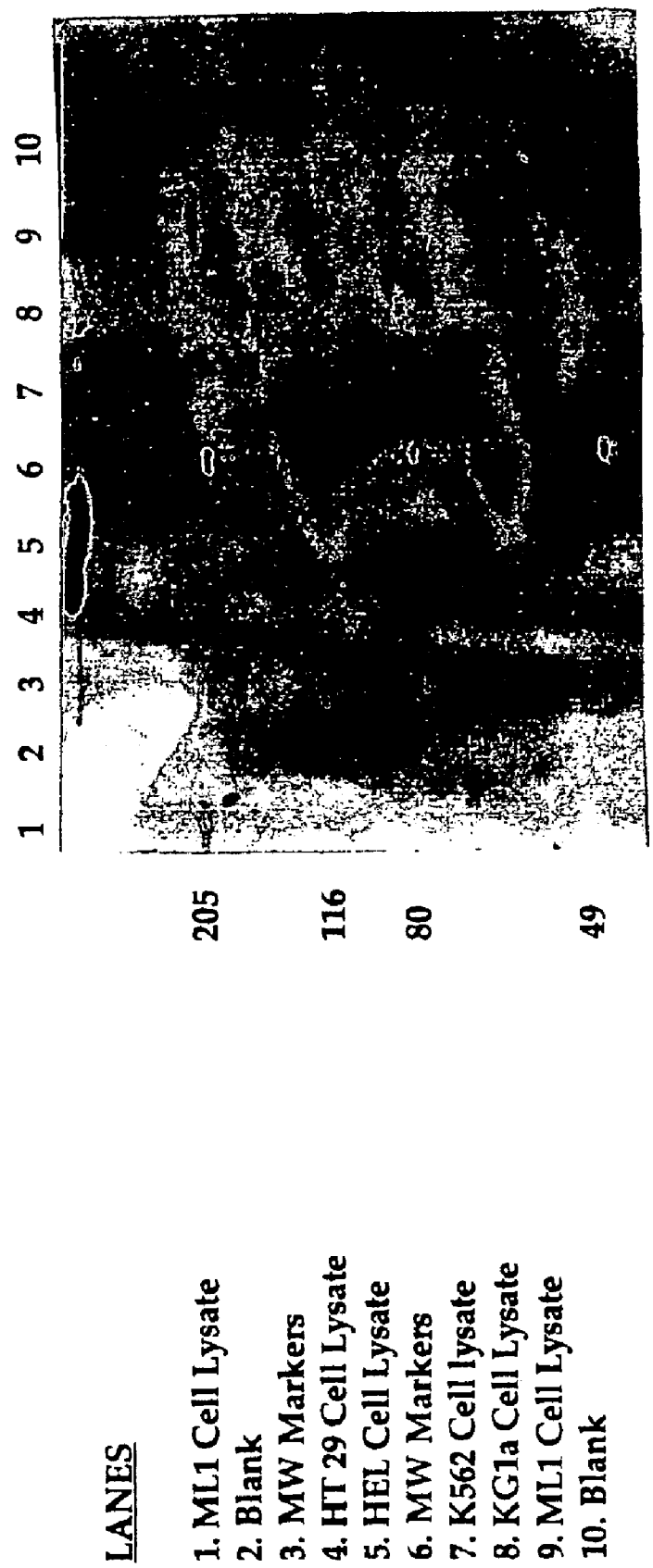
FIG. 6 shows hybridization of Western blot with MG1 hybridoma supernatant. Cell extracts from $10^6$ cells, prepared from various cell lines, were separated by SDS PAGE through 10% gels, and transferred to nitrocellulose membranes. The membrane was hybridized to MG1 primary antibody (hybridoma supernatant at a 1:10 dilution), and HRP-conjugated sheep anti-mouse IgG secondary antibody, and visualized by ECL. Marker: BioRad low range prestained markers: the positions of the 106, and 80 kDa bands are indicated with hyphens. ML-1; NSC1.1 cell extracts. HT-29, HEL, K562, and KG1a, refer to cell extracts from the respective cell lines.
Figure 7:
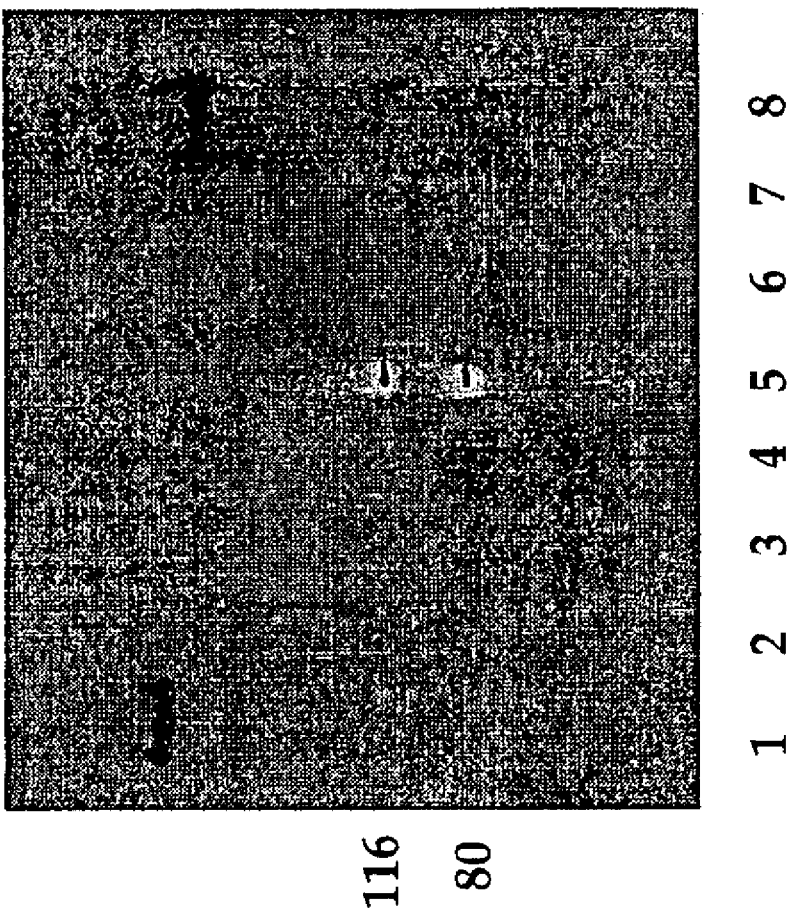
FIG. 7 shows hybridization of Western blot with MG1 purified antibody. Comparison with FIG. 6 shows that the purified antibody and hybridoma supernatant recognize the same protein in cell extracts. Cell extracts from $10^6$ cells, prepared from various cell lines, were separated by SDS PAGE through 10% gels, and transferred to nitrocellulose membranes. The membrane was hybridized to MG1 primary antibody (purified IgG), and HRP-conjugated sheep anti-mouse IgG secondary antibody, and visualized by ECL. Marker: BioRad low range prestained markers: the positions of the 106, and 80 kDa bands are indicated with hyphens. ML-1; NSC1.1 cell extracts. HT-29, HEL, K562, and KG1a, refer to cell extracts from the respective cell lines.

Western blot analysis was performed with two purposes in mind: First, to understand the scope of MG1's reactivity on different cell populations and second, to identify the ligand to which MG1 binds. Using lysates prepared from the leukemia cell lines (KG1a, K562, and HEL 92.1.7), western blot analysis was carried out, the results of which are shown in FIG. 5 (western blot using MG1 hybridoma supernatant-$\frac{1}{10}$ dilution), FIG. 6 (western blot using MG1 hybridoma supernatant-$\frac{1}{100}$ dilution) and FIG. 7 (western blot using purified MG1 IgG2a). The data from FIGS. 5–7 demonstrate that the only reactivity obtained was MG1 binding to the NSC1.1 lysate (lanes 2 and 9 of FIG. 5, lanes 1 and 9 of FIG. 6, and lanes 2 and 9 of FIG. 7). These results confirm the earlier flow data (FIG. 3) in which the MG1 monoclonal antibody only bound to the surface of the NSC1.1 cell and not to any of the cell lines mentioned above. The second observation to be made from FIGS. 5–7 is that the protein that is recognized by MG1 is a high molecular weight protein with a calculated (regression analysis) molecular weight of approximately 186 kDa±5%. Finally, a comparison of FIGS. 6 and 7 show that the hybridoma supernatant and the purified IgG from the monoclonal hybridoma recognize the same protein in Western analyses. This confirms the derivation of the monoclonal.

Figure 8:
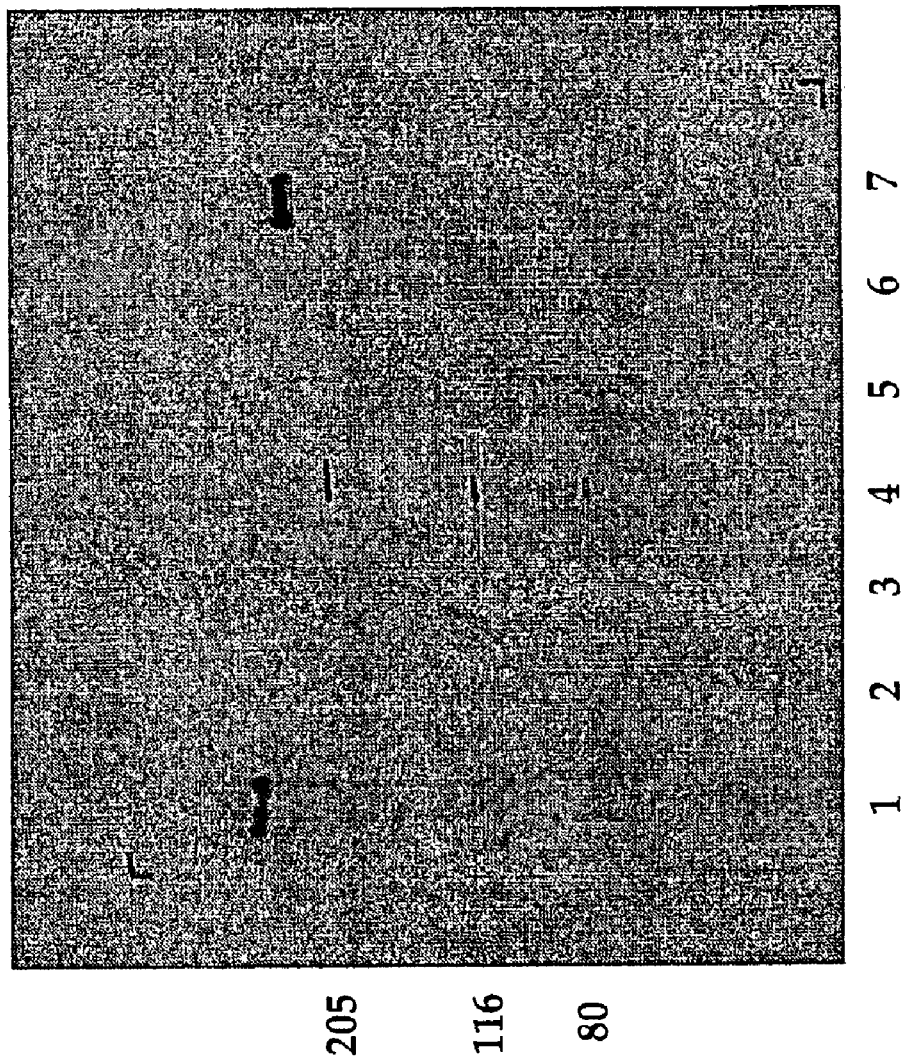
FIG. 8 shows hybridization of blood cell extracts with MG1 antibody. Cell extracts from NSC1.1 cells or from different populations of blood cells separated over PER-COLL gradients, were separated by SDS PAGE through 10% gels, and transferred to nitrocellulose membranes. The membrane was probed with purified MG1 IgG as primary antibody, and HRP-conjugated sheep anti-mouse IgG secondary antibody, and visualized by ECL. ML-1 lysate; lysate from $10^6$ NSC1.1 cells. RBCs, Granulocytes, Lymphocytes, Thrombocytes; lysates prepared from $10^5$ red blood cells, granulocytes, lymphocytes and thrombocytes, respectively. Marker: BioRad high range prestained markers; the positions of the 205, 116, and 80 kDa bands are indicated as short lines.

Similar western blot experiments were carried out using cell lysates from subpopulations of peripheral blood leukocytes enriched on self generated PERCOLL gradients. The blots were again probed with purified MG1 monoclonal antibody (14 $\mu$g). The data from FIG. 8 conclusively show that the MG1 antibody probe only recognizes NSC1.1 lysate (lanes 1 and 10) and does not recognize proteins associated with cells isolated from normal peripheral blood. Again, the protein recognized by MG1 antibody appears to have a molecular weight of approximately 186 kDa±5%.

Therefore, combining all the data from the western blot analyses and the flow cytometry together, it is believed that the MG1 monoclonal antibody recognizes a cell surface antigen that is only expressed on rare cells within the hematopoietic environment. Furthermore, given the CFU data, it is believed that these cells reside within the primitive stem cell compartment of that tissue.

EXAMPLE 2

Characterization of the MG1 Antigen

The MG1 antigen is expressed on a small proportion of human bone marrow cells, and this population overlaps with the $CD34^+$ population. MG1 and CD34 doubly labeled cells represented only minor subpopulations of the singly labeled cells. The results of flow analyses on bone marrow indicate that this overlapping population represents a small percentage of the $CD34^+$ population, and also a small percentage of the $MG1^+$ population. In other words, few of the CD34 population also labels with MG1, and few of the MG1 population also labels with CD34. The fact that independent flow studies showed that MG1 did not recognize any of the subpopulations of the peripheral blood leukocytes enriched on self generated PERCOLL gradients, suggests that MG1 is not recognizing mature cells. Furthermore, when MG1-selected cells are placed into CFU-GEMM assays (with cytokines IL-3, L-6, SCF and Epo), few if any colonies are detected, whereas the MG1-depleted population does generate colonies. This indicates that MG1 is not recognizing committed progenitor cells either. Recent results showing that high proliferative potential of hematopoietic cells is associated with quiescence in CFU assays (Berardi et al., *Science* 267:104–108 (1995); Young et al., *Blood* 87:545–556 (1996)) would suggest that the $MG1^+$ population falls into the category of very primitive, quiescent cells.

Figure 9:
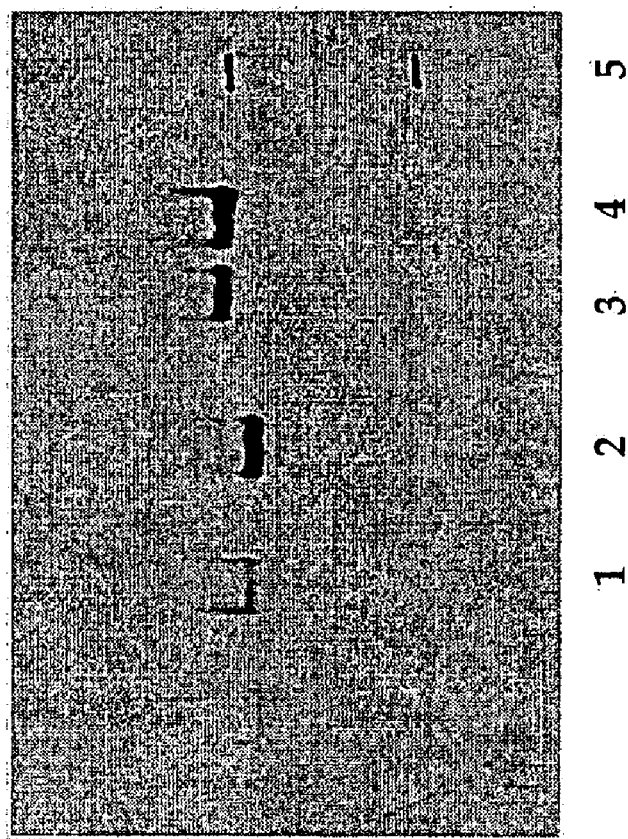
FIG. 9 shows a Western blot demonstrating that the MG1 antigen is glycosylated. 100 ml crude NSC1.1 lysate was incubated with the indicated glycosidases at 37° C. overnight. The samples were then diluted and separated by SDS PAGE through 10% gels, and transferred to nitrocellulose membranes. The membranes were hybridized to MG1 primary antibody, and HRP-conjugated sheep anti-mouse IgG secondary antibody, and visualized by ECL. Marker: BioRad high range prestained markers; the positions of the 205 and 116 kDa bands are indicated. Control; lysates incubated without enzyme. O-glycosidase; lysates incubated with 2.5 mU of O-glycosidase. N-glycosidase; lysates incubated with 6 units N-glycosidase. O+N-glycosidase; lysates incubated with both O- and N-glycosidases.

Glycosylation Determination of the MG1 antigen In order to characterize the MG1 antigen more fully, the protein was subjected to deglycosylation using glyconases specific for N-linked and O-linked carbohydrate moieties. It is evident from the data shown in FIG. 9 that the MG1 antigen is glycosylated and further, that this glycosylation is predominantly comprised of N-linked sugars (lane 2). Treatment of the MG1 antigen with O-glyconase did not measurably (as detectable by the resolving capability of this gel) decrease the molecular weight of the ligand (lane 3) indicating the lack of O-linked sugars. This was further confirmed by treatment of the MG1 antigen with a mixture of the two enzymes, the results of which are shown in lane 1 of FIG. 9, wherein the decrease in the molecular weight observed is equal to that of the N-glyconase treatment alone.

Figure 10:
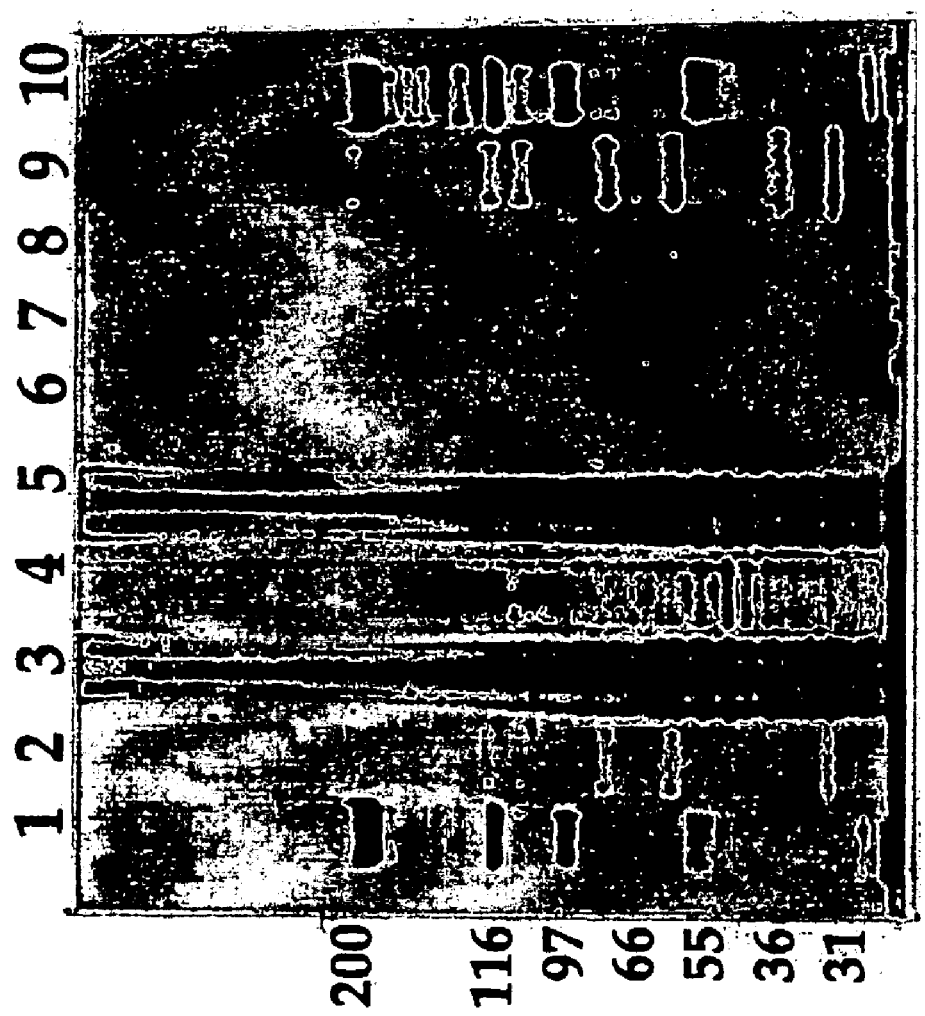
FIG. 10 shows partial purification of the MG1 antigen by affinity column chromatography. Lysates prepared from NSC1.1 cells were loaded onto an immunoaffinity column containing bound purified MG1 monoclonal antibody. The column was washed, and the bound protein was eluted with 0.1 M glycine (pH 2.7) into 1.0 M Tris (pH 9.0). This eluate was concentrated by ultrafiltration, and examined by SDS PAGE. The size of the MG1 antigen, as calculated by a regression analysis of the two protein marker lanes (non-prestained), is 186 kDa±5%. Legend: pm, prestained protein molecular weight markers; m, Novex 'Mark 12' protein molecular weight markers (The positions of the 200, 116.3, 97.4, 66.3, 55.4, 36.5, and 31.0 kDa bands are indicated); lys 1, aliquot of the NSC1.1 lysate, and lys 2, aliquot of a second protein extraction of the NSC1.1 lysate; f-t, the flow-through from loading the affinity column; elu, eluate; conc. elu, concentrated eluate; re-elu, second elution from the affinity column.
Figure 11:
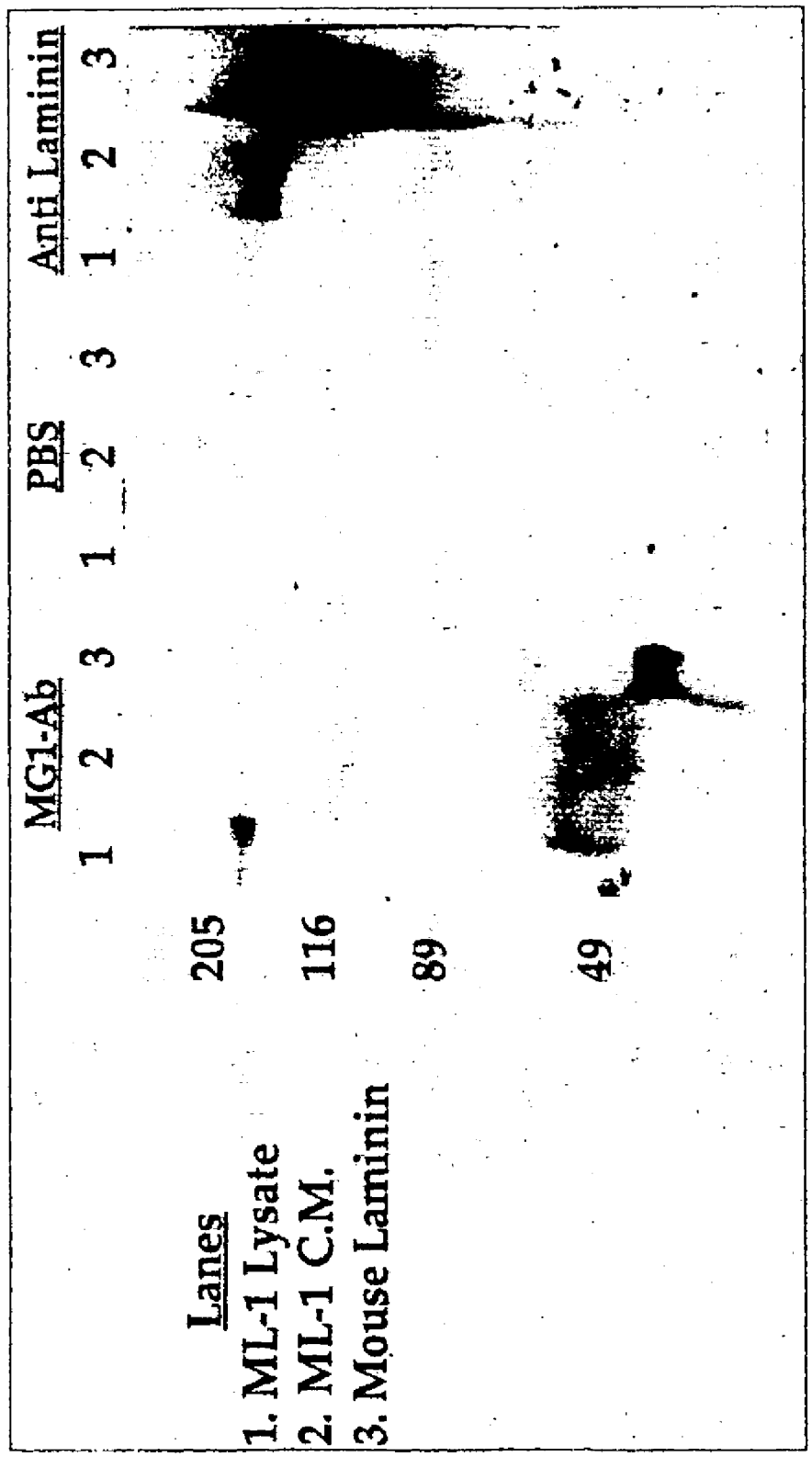
FIG. 11 shows a Western blot analysis for detection of laminin reactivity using NSC1.1 lysate and a polyclonal antibody against human laminin. NSC1.1 lysates (10 µl per lane), NSC1.1 conditioned medium (10 µl of condition medium concentrated 10× on a Centriprep column) and purified mouse laminin (approximately 21 µg per lane) were separated on SDS-PAGE through 10% gels and transferred to nitrocellulose membranes. The membrane was separated into three parts, and the individual parts hybridized to anti-laminin polyclonal antibody (1:2000 dilution), or MG1 monoclonal antibody (1/10 dilution), or PBS alone. Following incubation with the primary antibody, the membranes were washed, and horseradish peroxidase labeled goat anti-mouse (or donkey anti-rabbit) IgG secondary antibody was added (1/2000 dilution). Detection of antigen/antibody complexes was performed using the chemiluminescent reagent from Amersham's ECL system. The resulting X-ray films were developed using a Kodak M35A X-OMAT processor and the autoradiographs examined for positive reactions. The positions of the 205, 116, and 80 kDa bands of the BioRad high range prestained marker are indicated with short lines. Legend: ML-1 lysate, NSC1.1 lysates; ML-1 C.M., NSC1.1 conditioned medium; Miki, 1,2,3: lanes labeled with MG1 monoclonal primary antibody; PBS, 1,2,3: no primary antibody; polyclonal laminin Ab, 1,2,3: lanes labeled with anti-laminin polyclonal antibody.

Purification of the MG1 antigen The MG1 antigen was partially purified by affinity column chromatography. Lysates prepared from NSC1.1 cells were loaded onto an immunoaffinity column containing bound purified MG1 monoclonal antibody. The column was washed, and the bound protein was eluted with 0.1 M glycine (pH 2.7) into 1.0 M Tris (pH 9.0). This eluate was concentrated by ultrafiltration, and examined by SDS PAGE. The size of the MG1 antigen, as calculated by a regression analysis of the two protein marker lanes in FIG. 10 (non-prestained), was about 186 kDa±5%.

Reactivity with Laminin The amino acid composition of the purified ligand was determined (see Table 2) and compared to other previously described proteins in available databases using two different computer programs (ExPASy and Propsearch).

TABLE 2

AMINO ACID COMPOSITION FOR MG1 ANTIGEN

| Amino Acid | Percent of Total |
|---|---|
| Asx | 12.81 |
| Glx | 15.47 |
| Ser | 5.34 |
| His | 3.37 |
| Gly | 11.64 |
| Thr | 4.34 |
| Ala | 6.92 |
| Pro | 5.43 |
| Tyr | 2.56 |
| Arg | 4.12 |

TABLE 2-continued

AMINO ACID COMPOSITION FOR MG1 ANTIGEN

| Amino Acid | Percent of Total |
|---|---|
| Val | 6.06 |
| Met | 0.71 |
| Ile | 4.92 |
| Leu | 6.85 |
| Phe | 3.17 |
| Lys | 6.29 |

Results indicated that the MG1 antigen appeared to be a unique and novel protein. However, both programs found a low degree of similarity with β1 subunit of human laminin. In order to examine the possibility that the MG1 antigen could be the β1 subunit of human laminin, a Western blot analysis was conducted using NSC1.1 lysate and a rabbit polyclonal antibody against human laminin (FIG. 11). The results indicated that the anti-laminin antibody did not recognize any proteins in the NSC1.1 lysate suggesting that the MG1 antigen is not the β1 subunit of human laminin.

N-terminal amino acid sequencing of purified MG1 antigen was also performed. The partial amino acid sequence of the MG1 antigen is shown below (in standard three letter amino acid code):

ArgArgArgAlaLysGlnAsnGlnXaaGlyGluIle (SEQ ID NO. 1)

(where Xaa represents an undetermined residue). Since no other previously described proteins showed significant sequence identity with the amino acid composition and sequence of MG1 antigen, it was concluded that the MG1 antigen represents a novel protein.

It should be understood that the examples and embodiments described herein are for illustrative purposes only and that various modifications or changes in light thereof will be suggested to persons skilled in the art and are to be included within the spirit and purview of this application and the scope of the appended claims.

The entire disclosure of all publications (including patents, patent applications, journal articles, laboratory manuals, books, or other documents) cited herein are hereby incorporated by reference.

We claim:

1. A polynucleotide molecule that encodes a polypeptide, or a fragment or variant thereof, expressed on the surface of a subset of human hematopoietic mononuclear cells, wherein said polypeptide immunoreacts with MG1 antibody.

2. The polynucleotide according to claim 1, wherein said polypeptide comprises the amino acid sequence of SEQ ID NO. 1.

3. A human cell population substantially enriched for hematopoietic cells expressing the MG1 antigen and substantially free of mature myeloid and lymphoid cells.

4. The cell population according to claim 3, wherein said MG1 antigen immunoreacts with MG1 antibody produced by the hybridoma cell line deposited under ATCC Accession No. HB12232.

5. The cell population according to claim 3, wherein said MG1 antigen comprises the amino acid sequence of SEQ ID NO. 1.

6. A method for treating a malignant tumor in a patient, said method comprising administering an effective amount of an antibody to said patient that binds to an MG1 antigen.

7. The method according to claim 6, wherein said antibody is conjugated with a toxic molecule capable of killing or inhibiting the replication of a human cell.

8. The method according to claim 7, wherein said toxic molecule is selected from the group consisting of ricin, exotoxin, and diphtheria toxin.

9. The method according to claim 6, wherein said malignant tumor is leukemia.

10. The method according to claim 6, wherein said MG1 antigen immunoreacts with MG1 antibody.

11. The method according to claim 6, wherein said MG1 antigen comprises the amino acid sequence of SEQ ID NO. 1.

12. A method for providing genetic therapy for a condition treatable by gene therapy, said method comprising selecting a population of human cells substantially enriched for hematopoietic cells expressing an MG1 antigen, and introducing into the genome of said selected cell population a gene or polynucleotide molecule that can provide genetic therapy to correct or ameliorate said condition.

13. The method according to claim 12, wherein said cells substantially enriched for hematopoietic cells expressing said MG1 antigen are selected by (a) contacting a human cell suspension with an antibody that binds the MG1 antigen; and (b) recovering those cells which are bound by said antibody.

14. The method according to claim 13, wherein said cells substantially enriched for hematopoietic cells expressing said MG1 antigen are selected using an antibody designated as MG1 and produced by the hybridoma cell line deposited under ATCC Accession No. HB12232.

15. The method according to claim 13, wherein said cells containing said introduced gene or polynucleotide molecule are infused into a patient having a condition treatable by such genetic therapy.

16. A method for providing genetic therapy for a condition treatable by gene therapy, said method comprising administering an effective amount of a gene therapy vector to a person in need of such treatment, said vector comprising an antibody that binds to an MG1 antigen and further comprising a gene or polynucleotide molecule that can provide genetic therapy to correct or ameliorate said condition, wherein said vector binds to target cells expressing said MG1 antigen and said gene or polynucleotide molecule that can provide genetic therapy is introduced into the genome of said target cell expressing said MG1 antigen.

17. The method according to claim 16, wherein said antibody is incorporated into a liposome vector, a poly-L lysine conjugate vector, or a viral vector which has been modified to express said antibody or proteins which would bind said antibody on the viral surface.

* * * * *